United States Patent [19]

Stern et al.

[11] Patent Number: 5,641,867
[45] Date of Patent: Jun. 24, 1997

[54] ANTIBODY WHICH SPECIFICALLY BINDS TO ENDOTHELIAL-MONOCYTE ACTIVATING POLYPEPTIDE II

[75] Inventors: David M. Stern, Great Neck, N.Y.; Matthias Clauss, Bad Nauheim, Germany; Janet Kao; Mark Kayton, both of New York, N.Y.; Steven K. Libutti, Fort Lee, N.J.

[73] Assignee: The Trustees of Columbia University in the City of New York, New York, N.Y.

[21] Appl. No.: 129,456

[22] Filed: Sep. 29, 1993

[51] Int. Cl.$^6$ .................................................. C07K 16/24
[52] U.S. Cl. .................................... 530/388.23; 530/389.2
[58] Field of Search .......................... 530/387.7, 387.9, 530/388.2, 388.23, 388.8, 388.85, 389.7, 389.2; 436/548, 547; 424/185.1, 277.1; 435/240.27

[56] References Cited

U.S. PATENT DOCUMENTS

| | | |
|---|---|---|
| 4,456,550 | 6/1984 | Dvorak et al. |
| 4,481,137 | 11/1984 | Ohnishi et al. |
| 4,650,674 | 3/1987 | Aggarwal et al. |
| 4,785,077 | 11/1988 | Kornbluth et al. |
| 4,863,727 | 9/1989 | Zimmerman et al. |
| 4,900,724 | 2/1990 | Kato et al. |
| 4,980,160 | 12/1990 | Goldberg et al. |

OTHER PUBLICATIONS

Jornvall, et al., *Proc. Natl. Acad. Sci.–USA* (Jan. 1982) 79(2)287–291.

Kao, et al., *J. Biol. Chem.* (Oct. 5, 1992) 267(28): 20239–20247.

DuBois, Appella et al., *Cancer Research* (Nov. 1980) 40: 4204–4028.

DuBois, Law, and Appella, *Proc. Natl. Acad. Sci. –USA* (Dec. 1982) 79:7669–7673.

Suffness et al., J. Natural Products, vol. 45, pp. 1–14 (1982).

Martin et al., Cancer Research, vol. 46, pp. 2189–2192, (1986).

Goding, Journal of Immunological Methods, vol. 39, pp. 285–308, (1980).

Noguchi et al., Biochemical and Biophysical Research Communications, vol. 160, No. 1, pp. 222–227 (1989).

Robins, Immunology in Plant Sciences, Linskens et al. (Eds), Springer–Verlag, New York, pp. 86–141 (1986).

Nawroth et al., J. Exp. Med, vol. 168, pp. 637–647 (1988).

Goodman, Basic & Clinical Immunology, Fudenberg et al., (Eds), Lange Medical Publications, Los Altos, California, pp. 32–40 (1976).

*Primary Examiner*—Paula K. Hutzell
*Attorney, Agent, or Firm*—John P. White

[57] ABSTRACT

This invention provides a purified endothelial monocyte activating polypeptide (EMAP II). It further provides a method of obtaining purified endothelial monocyte activating polypeptide (EMAP II), a method of making antibodies to it and a method of detecting it. This invention also provides an effector cell activating protein which contains an amino acid sequence homologous to RIGRIVT and a method of detecting same. This invention also provides a method of treating a tumor in a subject by administering an effective dose of endothelial monocyte activating polypeptide (EMAP II).

4 Claims, 17 Drawing Sheets

FIGURE 1A
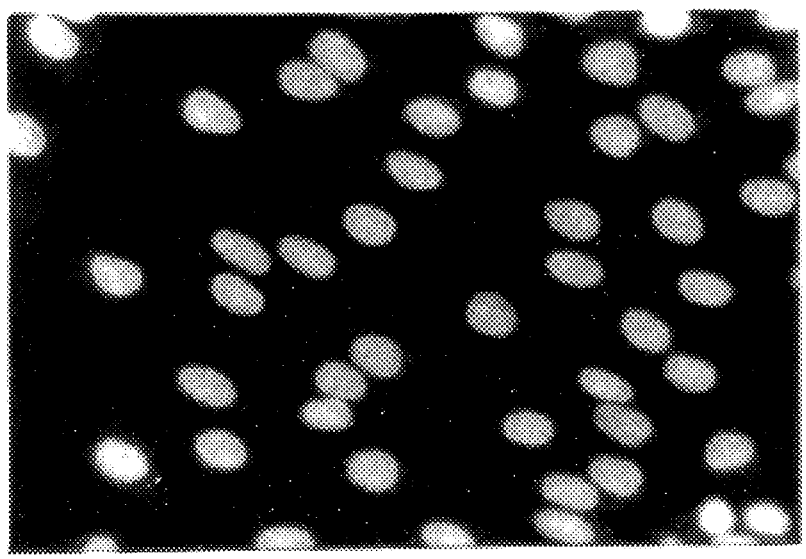
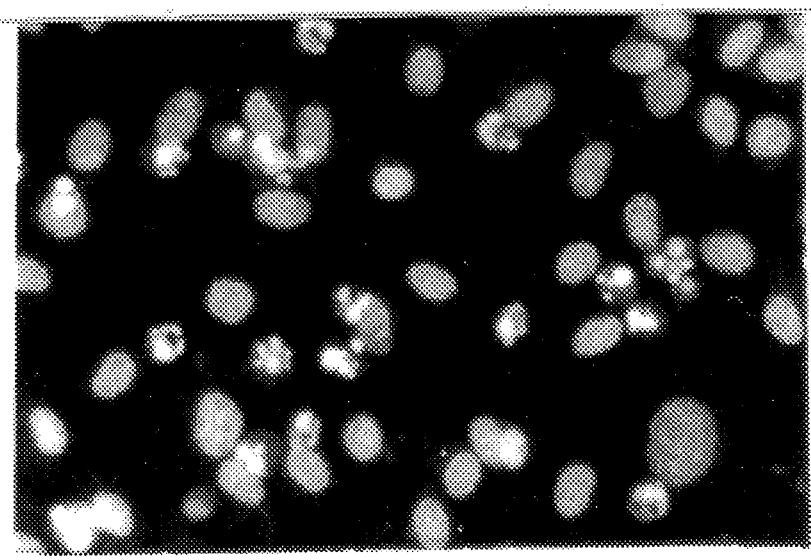
FIGURE 1B

FIGURE 2A
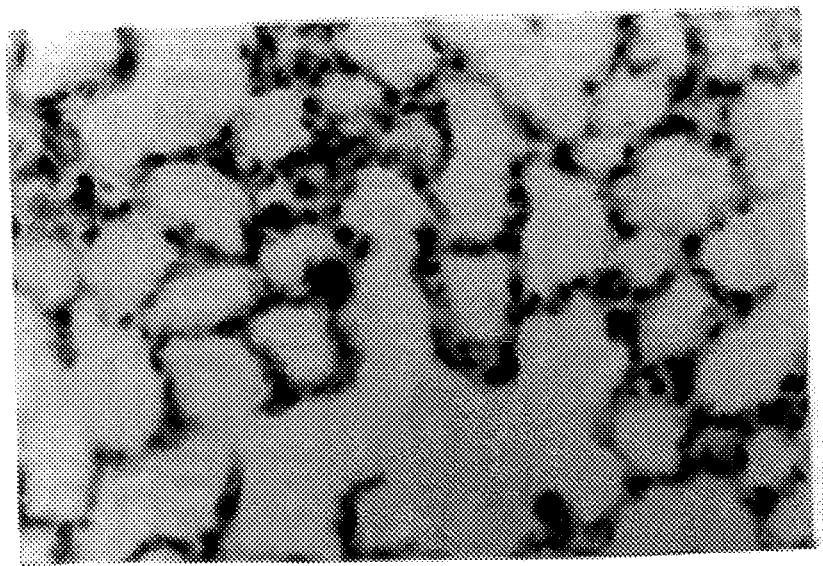
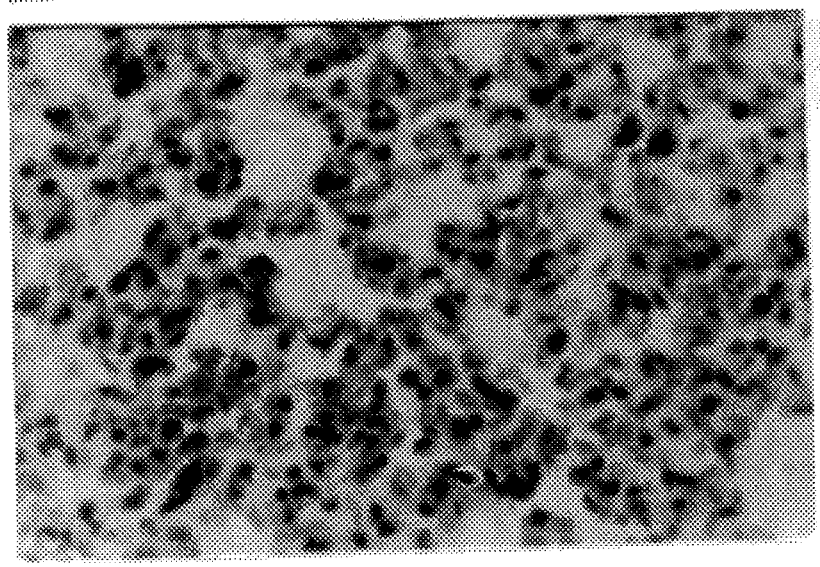
FIGURE 2B

FIGURE 3A
FIGURE 3B
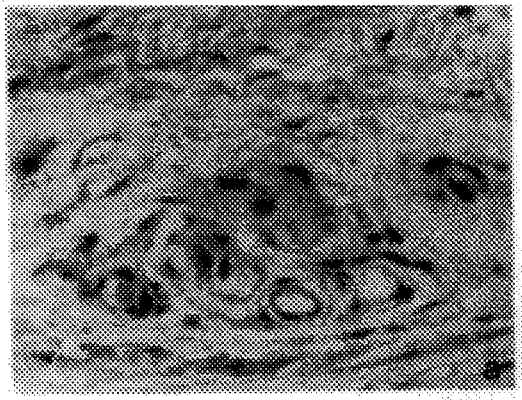
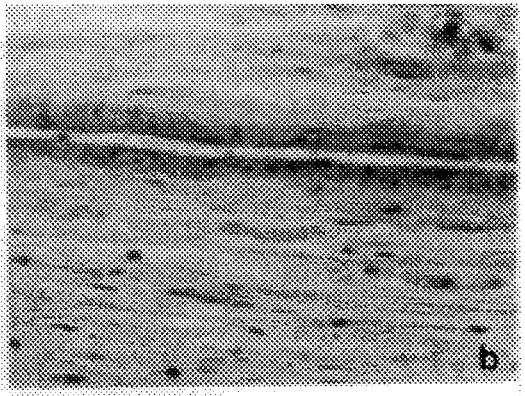
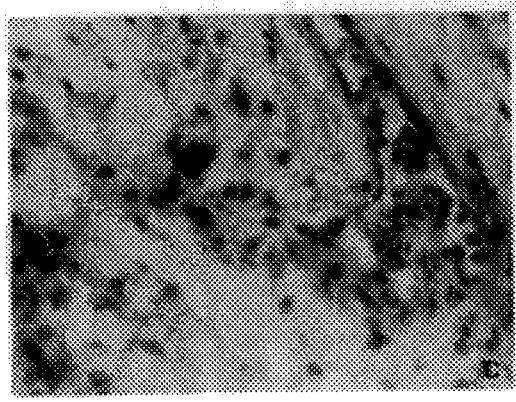
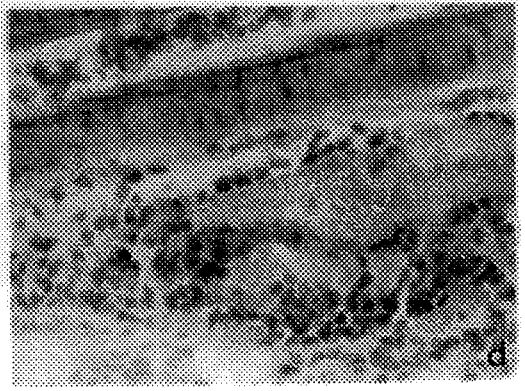
FIGURE 3C
FIGURE 3D

FIGURE 4A

```
                                                                                                      1
                                    GAGGCTGCTCAAGAGCTGCGGTTGGGTCACCGCTTCATGTTTCTGC

CGATTCTGGGGAAAG ATG GCA ACG AAT GAT GCT GTT CTG AAG AGG CTG GAG        99
murine       1          1   M   A   T   N   D   A   V   L   K   R   L   E     12
human        1          1   .   .   .   N   .   .   .   .   .   .   .   .     12

100
     CAG AAG GGT GCA GAG GCG GAT CAG ATC ATC GAA TAT CTC AAG CAG GTT          198
 13   Q   K   G   A   E   A   D   Q   I   I   E   Y   L   K   Q   V           45
 13   .   .   .   .   .   .   .   .   .   .   .   .   .   .   .   .           45

GCT CTT CTT AAG GAG AAA GCA ATT TTG CAG GCA ACA ATG AGA GAA GAA
 46   A   L   L   K   E   K   A   I   L   Q   A   T   M   R   E   E
 46   S   .   .   .   .   .   .   .   .   .   .   .   L   .   .   .

199
     AAG AAA CTT CGA GTT GAA AAT GCT AAA CTG AAA AAA GAA ATA GAA GAG CTA      297
 46   K   K   L   R   V   E   N   A   K   L   K   K   E   I   E   E   L       78
 46   .   .   .   .   .   .   .   .   .   .   .   .   .   .   .   .   .       78

AAG CAA GAG CTG ATT CTG GCA GAA ATT CAT AAC GGA GTG GAG CAA GTG
 K    Q   E   L   I   L   A   E   I   H   N   G   V   E   Q   V
 .    .   .   .   .   .   Q   .   .   .   Q   .   .   .   K   .   I
```

FIGURE 4B

```
     298
     CGT GTT CGA TTG AGT ACT CCA CTG CAG ACG AAC TGT ACT GCT TCT GAA AGT
 79   R   V   R   L   S   T   P   L   Q   T   N   C   T   A   S   E   S
 79   P   F   P   S   G   .   .   .   H   A   .   S   M   V   .   .   N
                                                                     396

GTG GTG CAG TCT CCA TCA GTA GCA ACC ACC GCC TCT CCT GCT ACA AAA
112   V   V   Q   S   P   S   V   A   T   T   A   S   P   A   T   K  111
111   V   .   .   I   .   T   A   .   .   .   V   .   S   G   .   .  110

397
     GAG CAG ATC AAA GCG GGA GAA GAA AAG GAG AAG GTG AAA GAG AAG ACT GAA AAG
112   E   Q   I   K   A   G   E   E   K   E   K   V   K   E   K   T   E   K
111   .   .   .   .   GGT .   D   .   .   .K   .   A   .   .   .   I   .   .

AAA GGA GAG AAA AAG GAG AAG CAG CAG TCG GCA GCA AGT ACT GAC
      K   G   E   K   K   E   K   Q   Q   S   A   A   S   T   D   144
      .   .   .   .   .   .   .   .   .   .   I   .   G   A   .   146
                                                                  →

496
     TCC AAG CCT ATC GAC GCA TCG CGT CTG GAT CTT CGA ATT GGT TGT ATT GTT
145   S   K   P   I   D   A   S   R   L   D   L   R   I   G   C   I   V
147   .   .   .   .   .   V   .   .   .   .   .   .   .   .   .   .   I
```

FIGURE 4C

```
                                                                          594
    ACT GCC AAG AAG CAC CCT GAT GCA GAT TCA CTG TAT GTG GAG GAA GTA  177
     T   A   K   K   H   P   D   A   D   S   L   Y   V   E   E   V   .
         .   R   .   .   .   .   .   .   .   .   .   .   .   .   .   179

595
    GAT GTG GGA GAA GCA GCC CCG CGC ACG GTC GTC AGC GGG CTG GTG AAT CAT
     D   V   G   E   A   A   P   R   T   V   V   S   G   L   V   N   H
178  .   .   .   .   A   .   .   .   .   .   .   .   .   .   .   .   .
180  .   .   .   .   I   .   .   .   .   .   .   .   .   .   .   .   .

693
    GTT CCT CTA GAA CAG ATG CAA AAT CGT ATG GTG GTT TTA CTC TGT AAT  210
     V   P   L   E   Q   M   Q   N   R   M   V   V   L   L   C   N   .
         .   .   .   .   .   .   .   .   .   .   .   I   .   .   .   212

694
    CTG AAG CCT GCA AAG ATG CGG GGA GTT CTG TCT CAA GCC ATG GTG ATG TGT
     L   K   P   A   K   M   R   G   V   L   S   Q   A   M   V   M   C
211  .   S   .   P   .   E   .   K   .   .   .   .   .   .   .   .   .
213  .   .   .   .   .   .   .   .   .   .   .   .   .   .   .   .   .

792
    GCC AGT TCA CCA GAG AAA GTG GAG ATT CTG GCC CCT CCC AAC GGG TCC  243
     A   S   S   P   E   K   V   E   I   L   A   P   P   N   G   S   .
         .   .   .   .   .   .   .   .   .   .   .   .   .   .   .   245
```

FIGURE 4D

```
       793
       GTT CCT GGG GAC AGA ATT ACT TTT GAT GCT TTT CCT GGA GAG CCT GAC AAG
244     V   P   G   D   R   I   T   F   D   A   F   P   G   E   P   D   K
246     .   .   .   .   .   .   .   .   .   .   .   .   .   .   .   .   .
                                                                    891
       GAG CTA AAC CCT AAG AAG ATC TGG GAG CAG ATC CAG CCT GAC CTG         276
        E   L   N   P   K   K   I   W   E   Q   I   Q   P   D   L         278
                .
       892
       CAC ACC AAT GCT GAG TGT GTG GCC ACA TAC AAA GGA GCT CCC TTT GAG GTG
277     H   T   N   A   E   C   V   A   T   Y   K   G   A   P   F   E   V
279     .   .   D   .   .   .   .   .   .   .   .   .   V   .   .   .   .
                                                                    990
       AAG GGG AAG GGA GTT TGC AGA GCC CAA ACC ATG GCC AAT AGT GGA ATT     309
        K   G   K   G   V   C   R   A   Q   T   M   A   N   S   G   I     311
                                                        S   .

991
       AAA TAA GTGCTCTGTAACTGAAAGACATTGGCGAAAACTTAATAACAATAAAGAGAAGTGTTT
310     K  stop
312     .

1086
       ATCACTTACATATAAAAAAAAAAAAAAAAAA
```

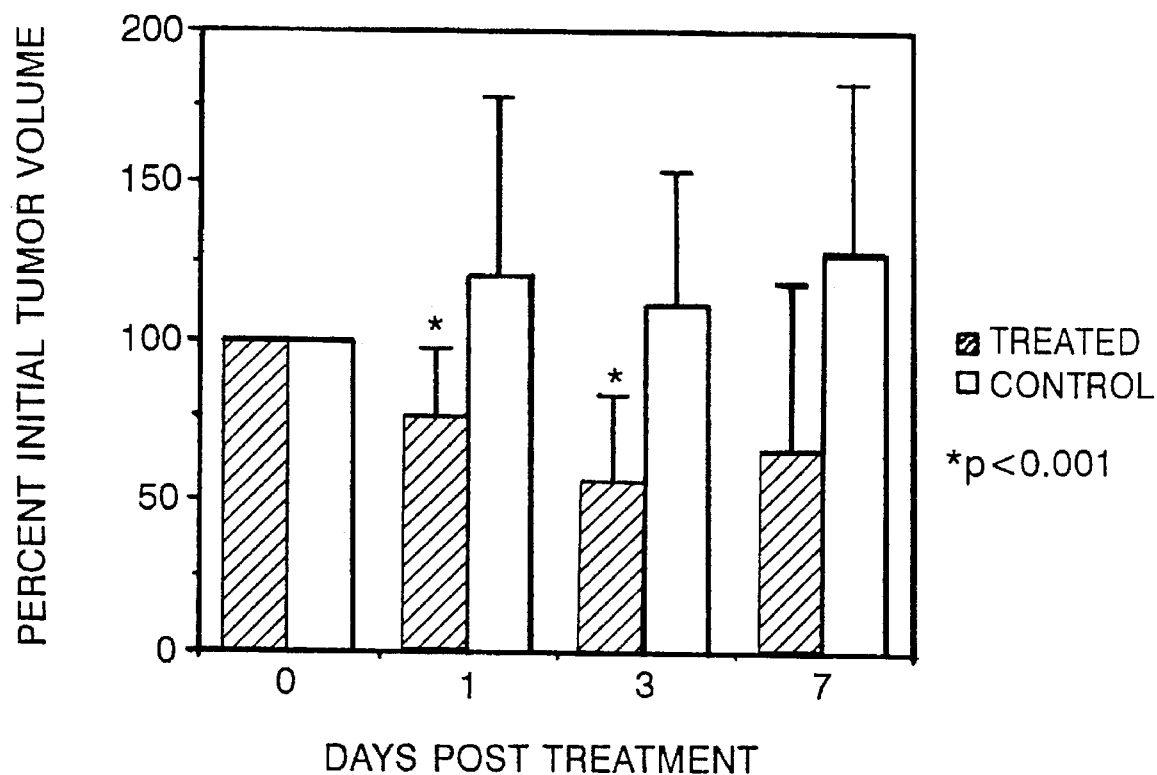

ANTIBODY WHICH SPECIFICALLY BINDS TO ENDOTHELIAL-MONOCYTE ACTIVATING POLYPEPTIDE II

The invention disclosed herein was made with Government support under NIH-PHS Grants Nos. HL02641, HL21006, HL42507, HL42833, and HL34625 from the Department of Health and Human Services. Accordingly, the U.S. Government has certain rights in this invention.

BACKGROUND OF THE INVENTION

Tumor vasculature is uniquely subject to the influence of products derived from the neoplastic cells. This may underlie the altered reactivity of vessels in certain tumors to catecholamines (1), tumor necrosis factor (TNF), flavone acetic acid (2), as well as other agents. To identify tumor-derived mediators which alter vascular function, the experiments described herein focussed on murine methylcholanthrene A (meth A)-induced fibrosarcomas. In vivo, this tumor is sensitive to TNF, and infusion of the cytokine at low concentrations results in vascular compromise localized to the neoplastic lesions with early thrombosis/hemorrhage in the vessels and increased vascular permeability, and later regression of the tumor (3–7). In contrast, cultured meth A tumor cells are relatively insensitive to TNF (3,8). This suggests that tumor-derived mediators, potentially acting at the level of the endothelium, a central regulator of vascular tone, permeability and thrombogenicity, could be important in host-tumor interactions.

These considerations have led to the study of supernatants of meth A fibrosarcoma cells in order to identify soluble factors which alter endothelial functions. Recently, the purification of an apparently unique polypeptide, $M_r \approx 40,000$, which alters endothelial and monocyte properties (Endothelial cell and Monocyte Activating Polypeptide, EMAP I) was reported (9–10). Reported here are the purification, N-terminal sequence, and characterization of another novel polypeptide from the same meth A fibrosarcoma supernatants, which alters endothelial and monocyte functions, induces the migration of monocytes and granulocytes, and induces an inflammatory response in the mouse footpad model. Because of these properties, this second polypeptide derived from meth A cells is termed endothelial-monocyte activating polypeptide II (EMAP II).

A prominent characteristic of immunogenic tumors is the presence of an inflammatory infiltrate surrounding the neoplastic lesion (103). One potentially important mechanism through which tumors modulate the host response is through the production of cytokines activating host effector cells, including mononuclear phagocytes (MPs), polymorphonuclear leukocytes (PMNs), and endothelial cells (ECs) (4–7). Using the murine methylcholanthrene A-induced fibrosarcomas (meth A) as a model system, three polypeptides with cytokine-like activities were identified (5–7). One of these is the murine homologue of vascular permeability factor/vascular endothelial growth factor (VPF/VEGF)(6) which modulates properties of ECs, including growth and induction of the procoagulant cofactor tissue factor, and MPs, including cell migration and tissue factor expression (8–13). In addition, two distinct polypeptides from meth A-conditioned medium termed endothelial-monocyte activating polypeptides I and II were isolated (5,7). EMAP II, a novel $\approx 20$ kDa polypeptide which has recently been cloned and is not a member of previously described cytokine/chemokine families, has multiple effects on ECs, MPs, and PMNs in vitro, and induces an acute inflammatory response upon subcutaneous injection into mice (7).

Protein sequence data from the N-terminal region of EMAP II (residues #10–20) indicated a close relationship to vonWillebrand factor antigen II (residues #480–490; 14–15), a molecule released by platelets and ECs along with vonWillebrand factor (16–17). Pilot studies with purified vonWillebrand antigen II showed that it had cytokine-like properties resembling EMAP II (18), leading to speculation that the region of strong sequence homology between the two molecules might mediate effects on target cells. Consistent with the possibility that the N-terminal position of EMAP II might be involved in its interaction with target cells is an homology to residues #31–37 of Interleukin (IL) 8, which includes the Glu-Leu-Arg motif associated with receptor binding and neutrophil activation by IL-8 (19–21). This study reports the synthesis of a series of peptides based on the N-terminal sequence of EMAP II (residues #6–20), and used these to perform experiments on cultured MPs and PMNs, and to inject into mouse footpads. The results support the hypothesis that this region of the molecule contributes to the functional activity of EMAP II. The N-terminal EMAP II-derived peptides interact with specific, potentially novel cellular binding sites, and may define a new ligand-receptor interaction important in tumor vasculature and inflammation.

SUMMARY OF THE INVENTION

This invention provides a purified endothelial monocyte activating polypeptide II (EMAP II).

This invention further provides a method of obtaining purified endothelial monocyte activating polypeptide II (EMAP II).

This invention provides a method of obtaining antibodies to purified endothelial monocyte activating polypeptide II (EMAP II).

This invention provides a method of detecting the presence of purified endothelial monocyte activating polypeptide II (EMAP II) in a sample.

This invention also provides an effector cell activating protein comprising a polypeptide having an amino acid sequence wherein at least four amino acid residues are the same as RIGRIVT (SEQ ID NO: 3) and are in the same relative positions.

This invention further provides a method of detecting the presence in a sample of effector cell activating protein.

This invention provides a method of treating a tumor in a subject comprising administering an effective dose of endothelial monocyte activating polypeptide II (EMAP II).

DESCRIPTION OF THE FIGURES

FIGS. 1A and 1B: Effect of EMAP II on migration and division of bovine aortic endothelial cells in an in vitro wound model. Confluent monolayers of BAE were stimulated to migrate and divide by removal of a ring fence creating a 5 mm diameter wound, at the time of wounding monolayers were exposed to EMAP II or control medium for 24 hours. Following incubation monolayers were washed, fixed in 3.5% paraformaldehyde in phosphate buffered saline containing 0.1% Nonidet P-40 and nuclei were stained with Hoechst 33258. Control monolayers migrating into the wound margin display normal interphase nuclei (FIG. 1A) compared with those exposed to EMAP, in which there are many condensed, pyknotic (apoptotic) nuclei (FIG. 1B). Wound margin is to the left.

FIGS. 2A and 2B: Infusion of EMAP II in murine inflammatory model. Mice were given intravenous injections of vehicle alone or vehicle containing EMAP via the tail vein and sacrificed by humane methods at 4 hours post infusion. Tissues were fixed in 10% formalin, processed routine methods and sections stained with hematoxylin and eosin. Lung from mice injected with vehicle alone are unremarkable (FIG. 2A) while those from mice exposed to EMAP display evidence of inflammation, mild edema, and cellular infiltrate (FIG. 2B).

FIGS. 3A–3D: Light micrographs of footpads inoculated with either EMAP II-derived peptide-albumin conjugates or albumin alone. Mouse footpads were injected with either albumin alone FIG. 3(A), albumin exposed to glutaraldehyde FIG. 3(B), albumin-RIGRIVTAKY (SEQ ID NO: 4) FIG. 3(C), or albumin-ASRLDLRIGRIVTAKY (SEQ ID NO: 6) FIG. 3(D). Following 6 hrs, footpads were harvested, processed as described in the text, and stained with hematoxylin/eosin. Magnification: x350.

FIGS. 4A–4D: Murine and Human EMAP II cDNA and EMAP II Sequence Derived Therefrom.

FIGS. 8A–8E: (A) Tumor Regression After EMAP II+TNF Treatment: Treated vs. All Controls; FIG. 8(B) Tumor Regression After EMAP II+TNF Treatment: Treated vs. H. T. EMAP II+TNF; FIG. 8(C) Tumor Regression After EMAP II+TNF Treatment: Treated vs. EMAP I +H. T. TNF; FIG. 8(D) Tumor Regression After EMAP II+TNF Treatment: Treated vs. H. T. EMAP II+H. T. TNF; FIG. 8(E) Tumor Regression After EMAP II+TNF Treatment: Treated vs. Vehicle+TNF

DETAILED DESCRIPTION OF THE INVENTION

Figure 5:
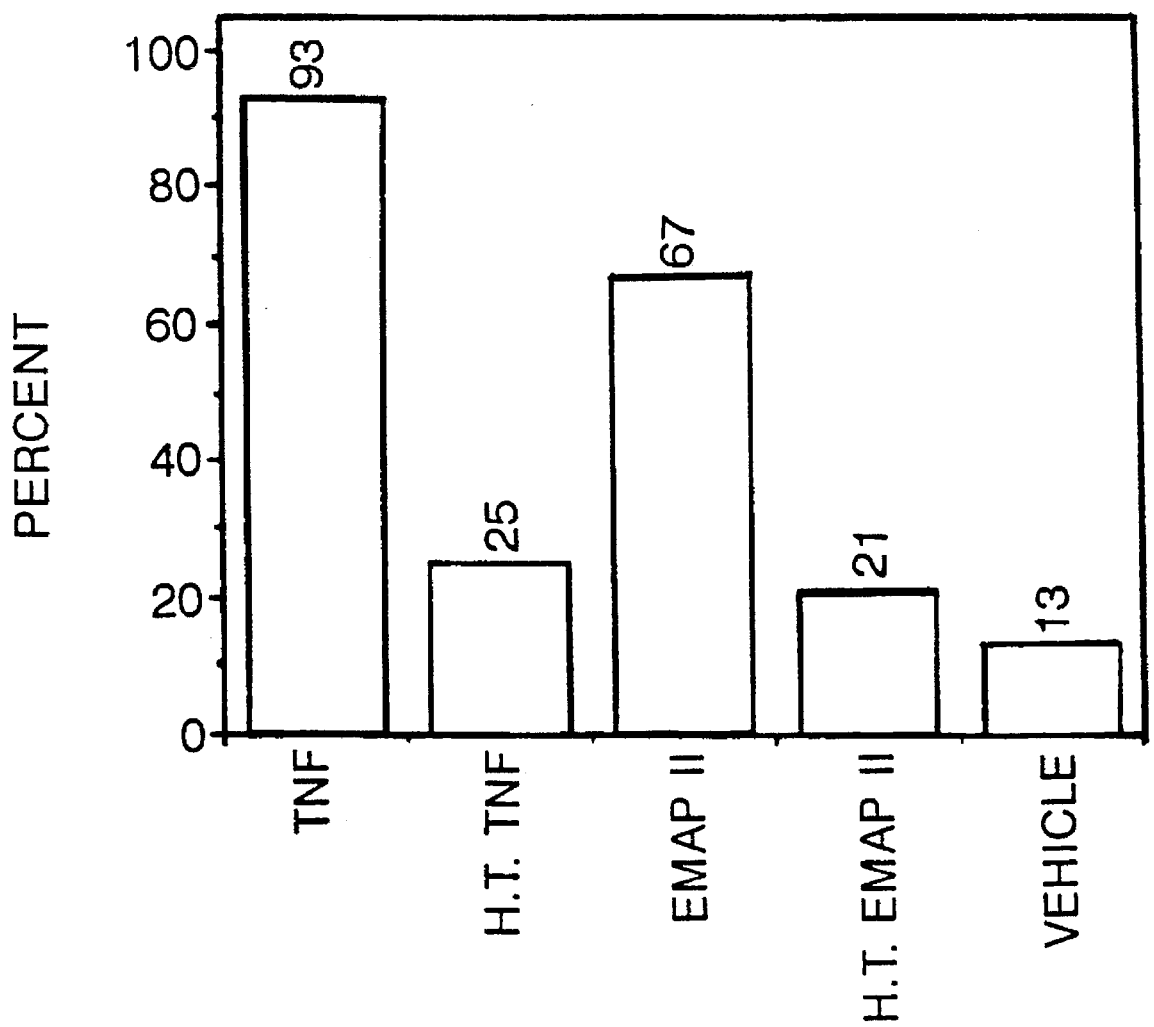
FIG. 5: Percentage of Meth A Tumors Demonstrating Gross Hemorrhage Six Hours After Single Injection

The following standard abbreviations are used throughout this application to refer to nucleosides and nucleotides:

| C = cytosine | A = adenosine |
|---|---|
| T = thymidine | G = guanosine |

The following standard single letter code abbreviations are used throughout this application to refer to amino acids:

| A, Ala; | C, Cys; | D, Asp; | E, Glu; | F, Phe; | G, Gly; | H, His; |
|---|---|---|---|---|---|---|
| I, Ile; | K, Lys; | L, Leu; | M, Met; | N, Asn; | P, Pro; | Q, Gln; |
| R, Arg; | S, Ser; | T, Thr; | V, Val; | W, Trp; | and Y, Tyr. | |

The following abbreviations are also used throughout this application:
TNF=tumor necrosis factor; vWF=von Willebrand Factor; PCR=polymerase chain reaction; EC=endothelial cell; EMAP=endothelial-monocyte activating polypeptide; VPF/VEGF=vascular permeability factor/vascular endothelial growth factor; GAPDH=glyceraldehyde phosphate dehydrogenase; fMLP=formyl-methionyl-leucinyl-phenylalanine; PMN=polymorphonuclear leukocyte; MP or mononuclear=mononuclear phagocyte; IL=interleukin; IL-I=interleukin 1; Meth A=methylcholanthrene A-induced murine fibrosarcoma; TMB=3,3',5,5'-tetramethylbenzidine; DSS=disuccinimidyl suberate; $[Ca^{2+}]_i$=cytosolic free calcium concentration.

Throughout this application, various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

This invention provides a purified endothelial monocyte activating polypeptide II (EMAP II).

This invention further provides an endothelial monocyte activating polypeptide II (EMAP II) having an apparent molecular weight of about 20,000 Daltons. More particularly, the EMAP II has an apparent molecular weight between about 18,000 Daltons and about 22,000 Daltons.

In a specific embodiment of this invention the endothelial monocyte activating polypeptide (EMAP II) is murine endothelial monocyte activating polypeptide (EMAP II).

In an embodiment of this invention endothelial monocyte activating polypeptide II (EMAP II) comprises the sequence Gly-Lys-Pro-Ile-Asp-Ala-Ser-Arg-Leu-Asp-Leu -Arg-Ile-Gly-Xaa-Ile-Val-Thr-Ala-Lys (SEQ ID NO: 1). In a specific embodiment, Gly-Lys-Pro-Ile-Asp-Ala-Ser-Arg-Leu-Asp -Leu-Arg-Ile-Gly-Xaa-Ile-Val-Thr-Ala-Lys (SEQ ID NO: 1) is the sequence of the N-terminal twenty amino acid residues.

This invention provides an antibody capable of binding to endothelial monocyte activating polypeptide II. This antibody may be a polyclonal antibody. Alternatively, it may be a monoclonal antibody.

This invention further provides a method of obtaining purified endothelial monocyte activating polypeptide II comprising, a) obtaining conditioned medium containing Meth A cells; b) purifying the medium from Meth A cells; c) applying the purified medium to a cation exchange resin; d) step-eluting from the cation exchange resin and pooling fractions with $OD_{280}>0.05$; e) applying the pooled fractions to an FPLC column; and f) eluting with an ascending salt gradient, thereby obtaining purified endothelial monocyte activating polypeptide II.

This invention also provides a method of obtaining an antibody to purified endothelial monocyte activating polypeptide II comprising a) immunizing a rabbit with Gly-Lys-Pro-Ile-Asp-Ala-Ser-Arg-Leu-Asp-Leu-Arg-Ile -Gly-Cys-Ile-Val-Thr-Ala-Lys (SEQ ID NO: 2) coupled to keyhole limpet hemocyanin; and b) obtaining purified IgG from the rabbit. In a specific embodiment, the antibody is a polyclonal antibody.

This invention provides a method of detecting the presence in a sample of EMAP II comprising a) adding cells to a to a first chamber; b) adding the sample to a second chamber which is separated from the first chamber by a membrane; c) visualizing migrating cells; d) counting the migrating cells; and e) determining the presence of EMAP II. In an embodiment, the cells are mononuclear phagocytes. In another embodiment, the cells are polymorphonuclear leukocytes.

This invention also provides a method of detecting the presence in a sample of EMAP II comprising a) injecting the sample into an animal footpad; and b) detecting an inflammatory response, thereby indicating the presence of EMAP II. In a preferred embodiment the animal footpad is a mouse footpad.

This invention also provides a method of detecting the presence in a sample of EMAP II comprising an immunoprecipitation step.

This invention also provides a method of detecting the presence in a sample of EMAP II comprising a) contacting cells with the sample; and b) assaying for tissue factor activity, thereby indicating the presence of endothelial monocyte activating polypeptide II. In a specific embodiment the cells are endothelial cells. In another specific embodiment the cells are monocytes.

This invention also provides a method of inducing chemotaxis comprising a) adding cells to a to a first chamber; and b) adding a chemotaxis-inducing effective amount of EMAP II to a second chamber which is separated from the first chamber by a membrane, thereby inducing chemotaxis of the cells. In an embodiment, the cells are mononuclear phagocytes. In another embodiment the cells are polymorphonuclear leukocytes.

This invention provides a method of inducing inflammation in a subject comprising injecting an inflammation-inducing effective amount of endothelial monocyte activating polypeptide II into the footpad of the subject. In a specific embodiment the subject is a mouse.

This invention also provides a method of inducing tissue factor comprising contacting cells with a tissue factor-inducing effective amount of endothelial monocyte activating polypeptide II. In a specific embodiment the cells are endothelial cells. In another specific embodiment the cells are monocytes.

This invention further provides an effector cell activating protein comprising a polypeptide having an amino acid sequence wherein at least four amino acid residues are the same as Arg-Ile-Gly-Arg-Ile-Val-Thr (RIGRIVT (SEQ ID NO: 3)) and are in the same relative positions. For example, AILRQVT (SEQ ID NO: 12) has at least four amino acid residues that are the same as RIGRIVT (SEQ ID NO: 3) and in the same relative positions because AILRQVT (SEQ ID NO: 12) matches RIGRIVT (SEQ ID NO. 3) in positions 2, 4, 6 and 7. The protein may have any number of amino acid residues as long as any seven-residue segment of the protein has at least four residues that are the same as RIGRIVT (SEQ ID NO: 3) and in the same positions relative to each other. For example, LAILRQVT (SEQ ID NO: 13) has four residues that are the same as RIGRIVT (SEQ ID NO: 3) and are in the same relative positions because LAILRQVT (SEQ ID NO. 13) matches RIGRIVT (SEQ ID NO: 3) at positions 3, 5, 7 and 8 of LAILRQVT (SEQ ID NO: 13). In contrast, RGRIVTI (SEQ ID NO: 14) has all residues the same as RIGRIVT (SEQ ID NO: 3) but only one residue is in the same relative position because RGRIVTI (SEQ ID NO: 14) matches RIGRIVT (SEQ ID NO: 3) only in position 1. In an embodiment, at least five amino acid residues are the same as RIGRIVT (SEQ ID NO: 3) and are in the same relative positions. In a more specific embodiment at least six amino acid residues are the same as RIGRIVT (SEQ ID NO: 3) and are in the same relative positions. A more specific embodiment comprises RIGRIVT (SEQ ID NO: 3).

In an embodiment the effector cell activating protein has at least seven amino acids. In a further embodiment the effector cell activating protein has between about 7 and about 16 amino acids.

In a specific embodiment, the effector cell activating protein is labeled. In an embodiment, the label is a radioactive label. In a preferred embodiment, the radioactive label is $^{125}$I.

In an embodiment of this invention, the effector cell activating protein comprises a polypeptide having an amino acid sequence selected from the group consisting of:
RIGRIVTAKY (SEQ ID NO: 4);
ASRLDLRIGCIVTAK (SEQ ID NO: 5);
ASRLDLRIGRIVTAKY (SEQ ID NO: 6);
ASRLDLRIGRIVTAK (SEQ ID NO: 7);
LRIGRIVTAKY (SEQ ID NO: 8);
RIGRIVT (SEQ ID NO: 3);
RIGRIIT (SEQ ID NO: 9); and
AIGRIVT (SEQ ID NO: 10).

In an embodiment, the effector cell activating protein is conjugated to an immobilizer. The immobilizer preferably comprises a polypeptide having a molecular weight of at least about 5,000 daltons. In a specific embodiment, the immobilizer is albumin.

This invention provides an antibody capable of binding to the effector cell activating protein. In a specific embodiment, the antibody is a polyclonal antibody. In another embodiment the antibody is a monoclonal antibody.

This invention further provides a method of obtaining an antibody to effector cell activating protein comprising a) immunizing a rabbit with the effector cell activating protein coupled to keyhole limpet hemccyanin; and b) obtaining purified IgG from the rabbit. In a specific embodiment the antibody is a polyclonal antibody. In another embodiment, the antibody is a monoclonal antibody.

This invention provides a method of detecting the effector cell activating protein.

This invention provides a method of detecting the presence in a sample of effector cell activating protein comprising a) adding cells to a first chamber; b) adding the sample to a second chamber which is separated from the first chamber by a membrane; c) visualizing migrating cells; d) counting the migrating cells; and e) determining the presence of the effector cell activating protein. In a further embodiment, the cells are mononuclear phagocytes. In another embodiment, the cells are polymorphonuclear leukocytes.

This invention also provides a method of detecting the presence in a sample of effector cell activating protein comprising the steps of a) injecting the sample into an animal footpad; and b) detecting an inflammatory response, indicating the presence in the sample of effector cell activating protein. In a specific embodiment of this method, the animal footpad is a mouse footpad.

A specific embodiment of the method of detecting the effector cell activating protein comprises a step of detecting binding to mononuclear phagocytes.

This invention provides a method of detecting the effector cell activating protein comprising a step of detecting increased $[Ca^{2+}]_i$ in effector cells. In a specific embodiment the effector cells are selected from the group consisting of mononuclear phagocytes and polymorphonuclear leukocytes.

This invention also provides DNA encoding the effector cell activating protein. This DNA may comprise the coding strand or the strand complementary to the coding strand. It may be single-stranded or double-stranded, circular or linear. It may further comprise promoters and other expression control sequences known to one with skill in the art to which this invention pertains. Because of the degeneracy of the genetic code, which is well known to one with skill in the art to which this invention pertains, various DNA sequences code for a single amino acid sequence.

In a specific embodiment, this invention provides DNA encoding the effector cell activating protein which comprises an amino acid sequence selected from the group consisting of:
RIGRIVTAKY (SEQ ID NO: 4);
ASRLDLRIGCIVTAK (SEQ ID NO: 5);
ASRLDLRIGRIVTAKY (SEQ ID NO: 6);
ASRLDLRIGRIVTAK (SEQ ID NO: 7);
LRIGRIVTAKY (SEQ ID NO: 8);
RIGRIVT (SEQ ID NO: 3);
RIGRIIT (SEQ ID NO: 9); and
AIGRIVT (SEQ ID NO: 10).

This invention provides a method of using the effector cell activating protein to induce cell chemotaxis. In a specific embodiment the cells are mononuclear phagocytes. In another specific embodiment the cells are polymorphonuclear leukocytes.

This invention provides a method of inducing chemotaxis comprising a) adding cells to a first chamber; and b) adding a chemotaxis-inducing effective amount of the effector cell activating protein of claim 27 to a second chamber which is separated from the first chamber by a membrane, thereby inducing chemotaxis of the cells. In a specific embodiment the cells are mononuclear phagocytes. In another specific embodiment the cells are polymorphonuclear leukocytes.

This invention further provides a method of inducing inflammation in a subject comprising administering an inflammation-inducing effective amount of the effector cell activating protein.

This invention also provides a method of increasing $[Ca^{2+}]_i$ in effector cells using the effector cell activating protein. In a specific embodiment the effector cells are selected from the group consisting of mononuclear phagocytes and polymorphonuclear leukocytes.

This invention further provides a method of treating a tumor in a subject comprising administering an effective dose of endothelial monocyte activating polypeptide II (EMAP II).

In a specific embodiment, this invention provides a method for treating the tumor by inducing hemorrhage in the tumor.

In another embodiment, this invention provides a method for treating the tumor by reducing the volume of the tumor. In a preferred embodiment, the volume of the tumor is reduced by at least twenty-five percent (25%).

In a specific embodiment, this invention provides a method of treating a methylcholanthrene A—induced fibrosarcoma tumor in a subject comprising administering an effective dose of endothelial monocyte activating polypeptide II (EMAP II). In a specific embodiment the subject is a mammal. In a more specific embodiment the subject is a mouse. In another specific embodiment, the subject is a human.

In a specific embodiment this invention provides a method of treating a tumor in a subject comprising administering an effective dose of endothelial monocyte activating polypeptide II (EMAP II) wherein the effective dose is between about two micrograms and about fifty micrograms. In a more specific embodiment the effective dose is about twenty micrograms. In another specific embodiment the effective dose is between about six micrograms and about one hundred fifty micrograms. In a more specific embodiment the effective dose is about sixty micrograms.

An embodiment of the method for treating a tumor in a subject further provides that the endothelial monocyte activating polypeptide II (EMAP II) is in a pharmaceutically acceptable carrier.

In an embodiment the administering comprises injecting intratumorally. In another embodiment, the administering further comprises administering systemically.

In a specific embodiment, the tumor comprises carcinoma cells. In a more specific embodiment the carcinoma cells are mouse mammary carcinoma cells.

Another embodiment further comprises administering an effective dose of tumor necrosis factor. Preferably, the effective dose of tumor necrosis factor is administered systemically. In a specific embodiment the effective dose is between about 500 nanograms and about fifteen micrograms. Preferably, the effective dose is about five micrograms.

In an embodiment this invention provides a method for treating a tumor in a subject wherein the tumor comprises carcinoma cells. In a specific embodiment the carcinoma cells are mouse mammary carcinoma cells.

This invention further provides the method for treating a tumor in a subject wherein the EMAP II is recombinant EMAP II.

This invention further provides the method for treating a tumor in a subject wherein the endothelial monocyte activating polypeptide II (EMAP II) comprises:

SKPIDASRLDLRIGCIVTAKKHPDADSLYVEEVDVGEAAPRTVVSGLV
NHVPLEQMQNRMVVLLCNLKPAKMRGVLSQAMVMCASSPEKVEILAPP
NGSVPGDRITFDAFPGEPDKELNPKKKIWEQIQPDLHTNAECVATYKG
APFEVKGKGVCRAQTMANSGIK(SEQ. ID NO: 11).

This invention further provides a pharmaceutical composition comprising an effective amount of endothelial monocyte activating polypeptide (EMAP II) in a pharmaceutically acceptable carrier. One of ordinary skill in the art will readily known how to select a pharmaceutically acceptable carrier for administration of EMAP II.

Experimental Details

This invention will be better understood from the Experimental Details which follow. However, one skilled in the art will readily appreciate that the specific methods and results discussed are merely illustrative of the invention as described more fully in the claims which follow thereafter.

A. ENDOTHELIAL MONOCYTE ACTIVATING POLYPEPTIDE II

MATERIALS AND METHODS

Culturing of cells and preparation of meth A-conditioned medium. Meth A cells, provided by Drs. Hoffman and Old (Memorial Sloan-Kettering Cancer Center) (11), were grown in RPMI 1640 containing 10% calf serum (Hyclone Labs, Logan, Utah) using a continuously perfused three liter bioreactor (Bellco Biotechnology, Vineland, N.J.). The bioreactor was washed with ten liters of serum-free medium (to remove serum components from complete medium), and then serum-free conditioned medium was collected at a rate of 416 ml/h, and concentrated 20-fold by ultrafiltration (12). Human umbilical vein endothelial cells (ECs) were prepared by the method of Jaffe (13), as modified by Thornton et al (14). Experiments were performed within 48 hours of the cells achieving confluence.

Purification of 22 kDa meth A factor. Following concentration of the conditioned medium from meth A cells by ultrafiltration, it was acidified to pH 5.5 with MES (1M), diluted 1:1 with 50 mM MES (pH 5.5), and applied to the cation exchange resin S-SEPHAROSE Fast Flow (Pharmacia, Piscataway, N.J.; 5 ml resin/liter). The resin was washed extensively in buffer containing MES (50 mM; pH 5.5), NaCl (50 mM), octyl-β-glucoside (0.1%) and PMSF (0.2 mM), and step-eluted with the same buffer supplemented with 1M NaCl. Fractions with $OD_{280}>0.05$ were pooled and dialyzed extensively versus phosphate buffer (50 mM); pH 5.5), NaCl (50 mM) and octyl-β-glucoside (0.1%). These procedures were performed at 4° C. The eluate from S-SEPHAROSE was then applied to an FPLC Mono S column (HR 5/5; Pharmacia) equilibrated in the same buffer, and the column was eluted with an ascending salt gradient. Fractions were incubated with cultured ECs, and assayed for their ability to induce tissue factor (see below). Active fractions eluting at 250 to 300 mM NaCl were pooled, dialyzed in the presence of SDS (0.1%), and concentrated by ultrafiltration (10 kDa-filter, Centricon, Amicon, Lexington, Mass.). Samples were then 1:1 diluted in nonreducing Laemmli sample buffer (15), incubated at 37° C. for 1 hr and preparative SDS-PAGE (12%) was performed. Following electrophoresis, protein was visualized by staining with Coomassie Blue or proteins were eluted by incubating gel slices for 48 hrs at 4° C. with buffer containing sodium acetate (0.1M; pH 8.3), octyl-β-glucoside (0.02%), azide (0.02%). Eluted proteins were incubated with ECs to test their ability to induce tissue factor (see below). In other cases, proteins in gels were visualized by silver staining using a kit (Biorad, Richmond, Calif.). For sequence analysis, purified ≈22 kDa meth A factor was subjected SDS-PAGE (12%), transferred to polyvinylidene difluoride membranes (16), and the broad band corresponding to Mr ≈22,000 was sequenced (Applied Biosystems, Inc. model 470A, Foster City, Calif.). The sequence was entered into the program WordSearch for the sequence analysis software package y Genetics Computer Group (17) to search the National Biomedical Research Foundation protein database. Other lanes from the same gel used for sequence analysis were transferred to nitrocellulose, proteins were eluted by the method of Anderson (18) and their ability to induce tissue factor in ECs was studied (see below).

Purified ≈22 kDa meth A factor was tested in the D10 bioassay for Interleukin 1 activity using the D10(N4)M cell line (19)(limit of detection 2 U/ml; generously performed by J. Plocinski and Dr. W. Benjamin, Hoffmann-LaRoche, Nutley, N.J.) and in the L929 assay for tumor necrosis factor activity (20) (limit of detection, 0.8 ng/ml; generously performed by J. DiPirro and Dr. J. Brentjans, SUNY, Buffalo, N.Y.). Neutralizing antibody to murine Interleukin 1α was obtained from Dr. R. Chizzonete (Hoffmann-LaRoche) and antibody to urine tumor necrosis factor was purchased from Genzyme (Cambridge, Mass.). Murine EMAP I and VPF/VEGF were prepared as described previously (9,22). Murine IL-1α was generously provided by Dr. P. Lomedico Hoffmann-LaRoche) and murine TNFα was obtained from Genzyme (Cambridge, Mass.).

Production and screening of polyclonal antibodies. Because only limited amounts of the ≈22 kDa polypeptide were available, a peptide based on the amino acid sequence was employed as immunogen. The peptide comprised the N-terminal sequence with Cysteine substituted for the undetermined amino acid at position 15 (see Table 1)(Multiple Peptide Systems, San Diego, Calif.) and an additional cysteine at the carboxy terminus to facilitate coupling to keyhole limpet hemocyanin using M-maleimidobenzoyl-N-hydroxysuccinimide (21). Rabbits were immunized by standard methods (initial immunization: 1 mg/animal; monthly boosts: 500 μg/animal; intradermal). Rabbit IgG, purified by affinity chromatography on protein A-SEPHAROSE (Pharmacia) (22), was screened by ELISA (Enzyme-Linked Immunosorbent Assay) using purified ≈22 kDa polypeptide. The ELISA was performed as follows: partially purified ≈22 kDa polypeptide or purified ≈22 kDa polypeptide in coating buffer ($Na_2CO_3$, 15 mM; $NaHCO_3$, 35 mM, $CaCl_2$, 0.1 mM; final pH 9.2) were incubated overnight at 4° C. in Nunc-Immuno Plate MAXISORP (Nunc-Kamstrup, Denmark). After 4 rinses in washing buffer (Tris/HCl, mM; NaCl, 120 mM; Tween 20, 0.05%; final pH 7.4), the primary antibody (3 μg/ml) was added for 1 hour at 37° C., wells were washed 4 times with washing buffer, and then incubated with peroxidase conjugated goat anti-rabbit IgG (Sigma, St. Louis, Mo.) at a 1:1000 dilution for an additional 1 hour at 37° C. Wells were washed 4 times, substrate solution (O-phenylenediamine dihydrochloride, 0.05 ml, 0.4 mg/ml, Sigma) dissolved in 0.1M sodium citrate (pH 4.5) containing H2O2 (0.0006%) was added, and color was allowed to develop. The reaction was stopped by adding $H_2SO_4$ (0.025 ml; 8N), and adsorbence at 490 nm was measured.

Western blotting and immunoprecipitation of ≈22 kDa meth A factor. Western blotting was performed using purified ≈22 kDa meth A-derived polypeptide, as well as other samples, by subjecting them to SDS-PAGE (12%) and electroblotting onto nitrocellulose paper (23). Reactive sites on the nitrocellulose were blocked overnight at room temperature with 3% nonfat dry milk in tris-buffered saline containing TWEEN 20(0.05%)(24). After 5 washes with the same buffer, nitrocellulose membranes were incubated for 2 hrs with polyclonal rabbit antibodies raised to the ≈22 kDa meth A factor 3 μg of immune IgG). Sites of primary antibody binding were detected with a secondary antibody conjugated to horseradish peroxidase using a kit from Amersham (Arlington Hts., Ill.). The approximate Mr of the meth A-derived polypeptide was estimated from the migration of standard proteins run simultaneously: phosphorylase b, 97.4 kDa, bovine serum albumin, 69 kDa, ovalbumin 46 kDa, carbonic anhydrase, 30 kDa, trypsin inhibitor, 21.5 kDa, and lysozyme, 14.3 kDa (Amersham).

Immunoprecipitation was performed by labelling cells metabolically with $^{35}$S-methionine as previously described (27). In brief, meth A cultures were incubated for 72 hrs in methionine-poor serum-free medium supplemented with $^{35}$S-methionine (10 μCi/ml), supernatants were harvested, diluted 1:1 with 50 mM MES (pH 5.5), applied to FPLC Mono S (HR 5/5; Pharmacia), and the column was then eluted with an ascending salt gradient (0 to 1M NaCl). The Mono S fractions which co-eluted with ≈22 kDa meth A factor, based on the studies described above (0.25–0.3M NaCl), were pooled, incubated overnight at 4° C. with immune or nonimmune IgG (5 μg/ml), and immune complexes were precipitated by the addition of formalin-fixed, protein A-bearing Staphylococcus aureus (IgGSorb, Enzyme Center, Malden, Mass.) for 2 hrs at room temperature. The immune precipitate was washed four times with tris-buffered saline (tris/HCl, 20 mM; pH 7.4; NaCl, 120 mM) containing NP-40 (0.25%), non-reducing Laemmli buffer was added, and the sample was boiled prior to SDS-PAGE.

Assays of endothelial cell and monocyte tissue factor. Tissue factor activity in human ECs was assayed by incubating confluent cultures (9.6 cm$^2$ growth area; ≈1. 2×10$^5$ cells/cm$^2$) with purified 22 kDa polypeptide in Medium 199 containing HEPES (10 mM; pH 7.4), polymyxin B (50 units/ml) and fetal calf serum (5%) in the presence/absence of other agents, such as either cycloheximide (10 µg/ml), actinomycin D (5 µg/ml), antibodies to the ≈22 kDa factor, or VPF/VEGF. Where indicated, ≈22 kDa meth A factor was treated with trypsin (5 µg/ml for 2 hr at 37° C.; trypsin was inactivated by addition of aprotonin, 25 µg/ml, Sigma) or heated (100° C. for 10 min; this destroys ≈22 kDa meth A factor activity, but has no effect on endotoxin-mediated induction of tissue factor activity) prior to addition to endothelial cell cultures. Monolayers were then incubated for the indicated times at 37° C., cells were scraped into suspension with a rubber policeman, and tissue factor activity was determined using a coagulant assay, as described previously (9,22). A blocking, monospecific antibody to tissue factor (2.5 µg/ml; generously provided by Dr. W. Kisiel, Univ. of New Mexico, Albuquerque, N.Mex.) was added to certain cell preparations just prior to performing the coagulant assay. Tissue factor equivalents were determined using a standard curve from experiments with purified human tissue factor (26). Tissue factor reconstituted into phosphati- dylserine/phosphatidylcholine vesicles (20:80) was generously provided by Dr. Ronald Bach, Univ. of Minnesota, Minneapolis, Minn.).

Procoagulant activity of mouse macrophages was determined as follows: suspensions of macrophages (10$^4$ cells/ assay), isolated from the peritoneum 3–4 days after stimulation with thioglycollate broth (2 ml; Sigma), were incubated with ≈22 kDa meth A factor alone or in the presence of other agents for the indicated times at 37° C. in RPMI 1640 containing HEPES (10 mM, pH 7.4), penicillin, streptomycin (50 U/ml; 50µg/ml), β-mercaptoaethanol (5×10$^5$M), and polymyxin B (50 units/ml). Tissue factor was determined as described above using the coagulant assay with murine plasma. Data are expressed as clotting time in seconds per sample assayed, since purified murine tissue factor is not available to use as a standard.

The level of tissue factor mRNA transcripts in human ECs and mononuclears exposed to ≈22 kDa meth A factor was studied using the polymerase chain reaction (PCR). For this purpose, total RNA was extracted from stimulated or quiescent cells using the guanidinium thiocyanate procedure (27). First strand cDNA was synthesized with oligo dT primer (BRL, Bethesda, Md.) and served as template for PCR analysis. Tissue factor primers were generously provided by Dr. W. Konigsberg (Yale University, New Haven, Conn.)(28) and GAPDH primers (29) were 5'CCA CCC ATG GCA AAT TCC ATG GCA (SEQ ID NO: 33) 3' (sense) and 5'TCT AGA CGG CAG GTC AGG TCC ACC (SEQ ID NO: 34) 3 (antisense)(synthesized in the Cancer Center Core Laboratory, Columbia Univ.). For positive controls, 10 pg of plasmid carrying tissue factor (provided by Dr. Konigsberg) sequence were used. cDNA was amplified by PCR for 20 to 40 cycles, each cycle consisting of incubations at 94° C. for 1.25 min, 50° C. for 1.25 min, and 72° C. for 2.25 min. Products were analyzed by agarose gel electrophoresis (2%) and were visualized with ethidium bromide under UV.

Assessment of mononuclear phagocyte (mononuclears) and polymorphonuclear leukocyte (PMN) migration. Human peripheral blood monocytes were isolated from the blood of normal healthy volunteers (30). Blood was centrifuged on HISOPAQUE 1077 (Sigma, St. Louis, Mo.), the mononuclear fraction was obtained, washed twice in Earle's balanced salt solution, resuspended in RPMI 1640 containing human serum (10%; Gemini, Calabasas, Calif.), plated on tissue culture dishes and incubated at 37° C. for 1–2 hrs. Nonadherent cells were removed by washing the plate twice with balanced salt solution, and adherent cells were harvested by incubation with calcium-magnesium free buffer containing EDTA (2 mM) for 15 min at 37° C., followed by extensive washing. PMNs were prepared by centrifugation over HISOPAQUE 1119 as per the manufacturer's protocol (Sigma). Chemotaxis assays were performed in microchemotaxis chamber (NeuroProbe, Bethesda, Md.) containing Nucleopore polycarbonate membranes (5 µm; Nucleopore, Pleasonton, Calif.). Mononuclears or PMNs were suspended in RPMI 1640 containing fetal bovine serum (1%) and 10$^4$ cells were added per well to the upper chamber. The chemotactic stimulus was added to the indicated chamber, and assays were performed in quadruplicate over a 3 hr or 45 min incubation period at 37° C., with mononuclear cells or PMNs, respectively, after which nonmigrating cells were removed, membranes were fixed in methanol, migrating cells were visualized with Wright's stain. Cells in nine high-power fields were counted, and the mean and standard error of the mean (SEM) were determined.

Mouse footpad studies. The potential in vivo effects of the ≈22 kDa meth A factor were assessed in the mouse foot pad model (31). In brief, footpads of female Balb/c mice (6–12 wks) were injected with ≈0.03 ml of either (i) Tris-buffered saline, ≈22 kDa meth A polypeptide (homogeneous, geleluted material), (ii) gel-eluted material from a region of the same SDS gel which had no ≈22 kDa meth A factor, (iii) V6,13 22 kDa meth A factor which had been pre-treated with trypsin (enzyme:substrate ratio, 1:50, w:w) for 1 hr at 37° C. followed by addition of aproptonin (0.5 ⇋g), or (iv) ≈22 kDa meth A factor was heat-treated at 100° C. for 10 min to destroy tryptic activity. At the indicated times footpad thickness was measured with calipers (each footpad was measured five times at each time point), and, subsequently, animals were sacrificed. Footpads were fixed in buffered formalin (10%), decalcified, and embedded in paraffin. Sections were stained with hematoxylin and eosin.

RESULTS

Purification of ≈22 kDa meth A factor (endothelialmonocyte activating polypeptide II [EMAPII]). In a previous study, two activities in conditioned medium from meth A fibrosarcomas which altered EC and mononuclear phagocyte properties were identified (9,10,22). The current report defines a third, novel meth A-derived polypeptide, distinct from those previously studied, which modulates endothelial and white cell functions.

Meth A-conditioned medium acidified, adsorbed to S-SEPHAROSE, and the bound material was step-eluted (1M, NaCl), dialyzed and applied to FPLC Mono S. The column was resolved with an ascending salt gradient, leading to the definition of three major peaks of activity, assessed by the induction of tissue factor activity in cultured ECs. The pool of fractions in activity peak I provided starting material for purification of EMAP I, a polypeptide with Mr ≈40,000, which was previously identified in tumor-conditioned medium (9,10). The material in activity peak III was used for preparation of murine Vascular Permeability Factor/ Vascular Endothelial Growth Factor (VEGF/VPF), and its activity could be neutralized by polyclonal antibody to guinea pig VPF, as described previously (22).

Activity peak II from the Mono S column was further analyzed by nonreducing SDS-PAGE, and elution of protein from nitrocellulose membranes after Western blotting. Although the pattern of protein bands visualized by Coomassie blue staining of the gels was complex, as expected form the chromatogram of the Mono S column, there were only two areas on the gel, corresponding to Mr ≈40,000 and ≈22,000, which on elution had the capacity to induce tissue factor activity in ECs. Since the higher molecular weight material was likely to correspond to EMAP I or VPF/VEGF, our attention was focussed on the factor(s) responsible for the activity at Mr ≈22,000.

To further characterized the material migrating with Mr≈22,000 which was responsible for induction of EC tissue factor, the corresponding portion of the nitrocellulose membrane was eluted, and subjected to SDS-PAGE. One broad band with Mr ≈22,000 was visualized by silver staining of nonreduced and reduced SDS-PAGE. Gel elution studies demonstrated that the material in the slices co-migrating with this band on non-reduced SDS-PAGE induced tissue factor activity in ECs. Following reduction or exposure to trypsin, this material lost its activity (data not shown).

Characterization of the ≈22 kDa polypeptide. The ≈22 kDa polypeptide was characterized structurally, by N-terminal sequencing, and immunologically, using an antiserum prepared to a peptide comprising the N-terminal sequence, in order to assess its relationship to other mediators present in the tumor-conditioned medium.

The broad band of SDS-PAGE with Mr≈22 kDa was transferred to PVDF and submitted for sequencing. Certain preparations ran as two closely spaced bands on SDS-PAGE, and both of these bands were transferred to PVDF and sequenced separately. In each case, identical preparations were transferred to nitrocellulose membranes, eluted, and demonstrated to induce tissue factor in ECs. The same N-terminal sequence was obtained each time (Table 1), and all samples displayed comparable capacity in the induction of EC tissue factor. Comparison of this sequence with others available in the database indicated that it was unique, with greatest homology to human von Willebrand antigen II (the propolypeptide region of vonWillebrand Factor)(32–33) (Table 1).

Mono S. Shorter exposure times of blots to the film showed that this major band was composed of two closely migrating bands. Addition of excess purified ≈22 kDa meth A factor during incubation of blots with the anti-peptide antibody greatly diminished intensity of the band, indicating that the antibody was recognizing determinants on EMAP II. Consistent with the specificity of the antibody for ≈22 kDa meth A factor, no bands were seen in blotting studies with EMAP I, VPF/VEGF, murine IL-1α or murine TNF. The distinction between ≈22 kDa meth A factor and the cytokines TNF and IL-1, both of which induce tissue factor in endothelium (34–37), was further supported by the finding that purified EMAP II had no IL-1 or TNF activity in sensitive bioassays (the D10 and L929 assays, respectively)(19–20), and that antibodies to these cytokines did not alter EMAP II activity.

To be certain that ≈22 kDa meth A factor was synthesized by the tumor cells, cultures were metabolically labelled with $^{35}$S-methionine, the supernatant was concentrated by cation exchange chromatography, and the eluate subjected to immunoprecipitation. Antipeptide IgG precipitated a band with Mr ≈22,000 from meth A tumor cells observed on both reduced and nonreduced SDS-PAGE. The appearance of this band was greatly diminished when excess ≈22 kDa meth A factor was added during incubation of reaction mixtures with the primary antibody, and no band was seen when immune IgG was replaced with non-immune IgG.

The IgG fraction of antiserum to the amino terminal peptide derived from the ≈22 kDa meth A factor was employed to construct an ELISA. This ELISA was used to monitor the purification procedure of the ≈22 kDa polypeptide (Table 2): about 195-fold purification was required to obtain homogeneous ≈22 kDa meth A factor with the series of steps used.

TABLE 1

Comparison of amino terminal sequence of ≈22 kDa meth A factor (EMAP II) with human von Willebrand Factor (vWF) antigen II.

EMAP II: Gly—Lys—Pro—Ile—Asp—Ala—Ser—Arg—Leu—Asp—Leu—Arg—Ile—Gly—Xaa—Ile—Val—Thr—Ala—Lys (SEQ ID NO: 1)

vWFII —Asp—Leu—Arg—Ile—Gln—Arg—Thr—Val—Thr—Ala—Ser—(SEQ ID NO: 15)

The portion of the vWF antigen II sequence shown corresponds to Asp (480) to Set (490), and was deduced from the cDNA (32–33).

Antibodies to the ≈22 kDa polypeptide were prepared by immunizing rabbits with a synthetic peptide comprising the amino terminal sequence coupled to keyhole limpet hemocyanin. IgG from this antiserum neutralized the ability of the ≈22 kDa meth A factor to induce tissue factor activity in ECs in a dose-dependent manner and adsorbed the activity when the antibody was bound to a solid support. In contrast, non-immune IgG was without effect.

Immunoblotting with IgG prepared to the synthetic peptide, following non-reduced SDS-PAGE, visualized a major band with Mr 22,000 in samples of purified ≈22 kDa meth A factor and fractions from activity peak II from FPLC

TABLE 2

Monitoring the purification procedure of ≈22 kDa meth A factor (EMAP II) by ELISA*.

| Total protein [mg] | EMAP II antigen [mg] | Sp. activity EMAP II antigen | Purification fold | Yield EMAPII antigen |
|---|---|---|---|---|
| Tumor supernatant | | | | |
| 150 | 0.77 | .00513 | 1 | 100% |
| Fast S, batch | | | | |
| 170 | 0.38 | .0223 | 4.4 | 50% |
| Mono S | | | | |
| 0.4 | 0.14 | .35 | 68.2 | 36% |

TABLE 2-continued

Monitoring the purification procedure of ≈22
kDa meth A factor (EMAP II) by ELISA*.

| Total protein [mg] | EMAP II antigen [mg] | Sp. activity EMAP II antigen | Purification fold | Yield EMAPII antigen |
|---|---|---|---|---|
| Gel elution 0.01 | 0.0095 | 1 | 195 | 6.8% |

*EMAP II antigen was measured using an ELISA, as described in the text. The starting volume of culture supernatant for this preparation was about 40 liters.

Functional characterization of ≈22 kDa meth A factor. To understand the potential contribution of the ≈22 kDa polypeptide to vascular dysfunction in the tumor bed and the inflammatory infiltrate which characteristically surrounds meth A tumors (3–6, 38–39), experiments were performed to assess its effects on ECs, mononuclear phagocytes, and polymorphonuclear leukocytes (PMNs).

Incubation of cultured human ECs with purified ≈22 kDa meth A factor led to a time-dependent, reversible increase in procoagulant activity which was maximal by 10–12 hrs, and then declined. Procoagulant induction was also dependent on the dose of ≈22 kDa polypeptide, being half-maximal by about 20–30 pM. Studies with a blocking monospecific antibody to tissue factor identified the induced EC procoagulant activity as tissue factor. Tissue factor expression required de novo biosynthesis, as demonstrated by inhibition in the presence of actinomycin D and cycloheximide. Consistent with the involvement of biosynthetic mechanisms, the level of transcripts for tissue factor mRNA increased on exposure to ≈22 kDa meth A factor, as indicated by the greater intensity of the PCR reaction product. In contrast, the level of transcripts for glycerceraldehyde phosphate dehydrogenase (GAPDH) mRNA in ECs was unchanged under these conditions. EMAP II-mediated induction of EC tissue factor was not likely to be due to contaminating endotoxin, as demonstrated by the inhibitory effect of antibody raised to the amino terminal EMAP II peptide and pre-treatment of the polypeptide with trypsin. In addition, all assays of endothelial procoagulant activity were performed in the presence of polymyxin B.

Mononuclear cells associated with tumors are often enmeshed in fibrin, suggesting that they might express procoagulant activity (38). Therefore, experiments were performed to examine if ≈22 kDa meth A factor could induce monocyte procoagulant activity. Incubation of murine peritoneal macrophages with EMAP II resulted in induction of procoagulant activity, as shown by the ability of the treated cells to shorten the clotting time of recalcified murine plasma. Induction of procoagulant activity occurred in a time-dependent manner, peaking at about 6–12 hours, and could be blocked almost completely by a monospecific antibody against human tissue factor, indicating that most of the clot promoting activity was due to tissue factor. Tissue factor expression by mononuclears in response to ≈22 kDa meth A factor was also dependent on the polypeptide's concentration, could be blocked by treating EMAP II with trypsin, and required the integrity of biosynthetic mechanisms, as it was prevented by addition of actinomycin D to cultures. Similar to the results on ECs described above, enhanced expression of mononuclear cell tissue factor activity was accompanied by an increase in the level of tissue factor mRNA transcripts, as evidenced by PCR.

Immunogenic tumors, such as the meth A fibrosarcoma, are often surrounded by an inflammatory infiltrate (38, 40–41). Experiments were performed to examine if the ≈22 kDa meth A polypeptide could induce migration of human PMNs and mononuclear cells harvested from peripheral blood (Tables 3–4). Experiments in microchemotaxis chambers demonstrated that EMAP II enhanced cell migration in a dose-dependent manner for PMNs (Table 3) and for mononuclear cells (Table 4). Cell migration in response to EMAP II was prevented by exposing the polypeptide to trypsin or by adsorption of EMAP II with polyclonal antibody to the N-terminal peptide. Checkerboard analysis in which the ≈22 kDa meth A factor was added to both the upper and lower compartments of the chambers indicated that enhanced migration was due to chemotaxis, not simply chemokinesis (Tables 3–4).

The effect of EMAP II on migration and division of bovine aortic endothelial cells in an in vitro wound model was also studied. Confluent monolayers of BAE were stimulated to migrate and divide by removal of a ring fence creating a 5 mm diameter wound, at the time of wounding monolayers were exposed to EMAPII or control medium for 24 hours. Following incubation monolayers were washed, fixed in 3.5% paraformaldehyde in phosphate buffered saline containing 0.1% Nonidet P-40 and nuclei were stained with Hoechst 33258. Control monolayers migrating into the wound margin display normal interphase nuclei compared with those exposed to EMAP, in which there are many condensed, pyknotic (apoptotic) nuclei (FIGS. 1A and 1B).

TABLE 3

Induction of polymorphonuclear leukocyte migration by ≈22 kDa meth A factor (EMAP II): checkerboard analysis*.

| Lower compartment | Upper compartment | | | |
|---|---|---|---|---|
| | 0 | 40 pM | 100 pM | 200 pM |
| 40 pM | 66 (S.D.7.8) | 50.5 (S.D.23.5) | 59 (S.D.19.8) | 52 (S.D.25.3) |
| 100 PM | 79 (S.D.22.9) | 63.6 (S.D.13) | 54 (S.D.17.4) | 58 (S.D.17.6) |
| 200 pM | 107 (S.D.29.8) | 95.7 (S.D.15.6) | 86.4 (S.D.23) | 57.8 (S.D.17.6) |

*Cell migration assays were performed by adding PMNs to the upper wells of microchemotaxis chambers, and placing the indicated concentration of ≈22 kDa meth A factor in the upper and/or lower wells. The incubation period was 45 min at 37° C. Migrating cells from nine representative high-powered fields are shown (the mean and standard deviation, S.D.).

TABLE 4

Induction of mononuclear cell migration by ≈22 kDa meth A factor (EMAP II): checkerboard analysis*.

| Lower compartment | Upper compartment | | | |
|---|---|---|---|---|
| | 0 | 50 pM | 100 PM | 200 pM |
| 50 pM | 18 (S.D.2.6) | 20 (S.D.3.7) | 15.7 (S.D.2.3) | 14.3 (S.D.1.2) |
| 100 PM | 30.4 (S.D.5.8) | 24.4 (S.D.2.6) | 19 (S.D.1.8) | 17.2 (S.D.2.6) |
| 200 pM | 53.78 (S.D.3.1) | 31.2 (S.D.1.2) | 18.7 (S.D.2.4) | 13.7 (S.D.0.8) |

*Cell migration assays were performed by adding mononuclear cells to the upper wells of microchemotaxis chambers, and placing the indicated concentration of kDa meth A factor in the upper and/or lower wells. The incubation period was 3 hr at 37° C. Migrating cells from nine representative high-powered fields are shown (mean and standard deviation, S.D.).

Phlogogenic properties of ≈22 kDa meth A-derived polypeptide (EMAP II) in the mouse footpad model. When EMAP II was injected into mouse footpads, swelling was observed as evidenced by the increase in footpad thickness compared with buffer controls. The footpad showed an acute inflammatory response characterized by a PMN infiltrate and edema in the subcutaneous tissues, compared with the untreated control. The inflammatory response had begun to recede by 8 hr after injection of EMAP II. In contrast to these results with intact EMAP II, trypsin-treatment of polypeptide abrogated its phlogogenic properties (FIGS. 2A and 2B).

DISCUSSION

Immunogenic tumors, such as the murine meth A fibrosarcoma, characteristically have a peripheral zone which contains a chronic inflammatory infiltrate (38–41). The presence of these inflammatory cells, often embedded in a meshwork of fibrin which can extend throughout the tumor stroma, contributes to the concept that tumors might be considered "wounds that do not heal (38)." This has led us to identify tumor-derived mediators which could prime the host response, altering endothelial properties and attracting inflammatory cells to the tumor. Previously, we presented the initial characterization of two polypeptides which, based on in vitro studies, could activate ECs and monocytes: EMAP I, a trypsin-sensitive, ≈40 kDa polypeptide distinct from other cytokines and growth factors (9–10), and a polypeptide which turned out to be the murine homolog of VPF/VEGF (22), a factor which had previously been shown to increase vascular permeability and to be mitogenic for ECs (42–46). In this report, a third polypeptide has been identified in supernatants of meth A tumor cells (EMAP II).

EMAP II activates ECs and mononuclear cells, potentiating their participation in procoagulant reactions through induction of tissue factor, promoting migration of monocytes and PMNs, and leading to a phlogogenic response when injected into murine footpads. EMAP II is an apparently unique polypeptide which runs as a broad band, Mr ≈22,000. In view of the apparently similar spectrum of biological properties of EMAP II and the other two mediators, VPF/VEGF and EMAP I, it was important to determine if there was a relationship between these molecules. Although the amino terminal sequence and chromatographic properties of EMAP II were distinct, it could represent an alternatively spliced or degraded form derived from the other polypeptides, which appear to be about twice as large, Mr 38–44 kDa versus ≈22 kDa. However, studies with polyclonal antibody directed against the amino terminal portion of EMAP II did not show any immunoreactivity with either EMAP I or VPF/VEGF. In addition, polyclonal antibodies which adsorb murine VPF/VEGF (22) did not react with EMAP II (data not shown). Furthermore, metabolic labelling and immunoprecipitation of meth A tumor cells demonstrated EMAP II to be synthesized as a ≈22 kDa polypeptide, no larger precursor form was evident. These findings are supported by functional studies which showed that EMAP II has distinct biologic activities compared with EMAP I and VPF/VEGF: EMAP II stimulates PMN migration, in contrast to the other two mediators, but EMAP II does not directly increase EC monolayer permeability in culture, whereas EMAP I and VPF/VEGF do. Finally, molecular cloning studies have shown EMAP II to be distinct from EMAP I, VPF/VEGF, and vWF antigen II. With respect to vWF antigen II, the region of sequence homology with EMAP II is limited to the portion of the amino terminus shown in Table 1. Taken together, these data suggest that EMAP II is a distinct molecule, capable of eliciting a phlogogenic response and, potentially, augmenting the effects of other tumor-derived cytokines.

An important and unexplained question concerning the production of inflammatory mediators by meth A, as well as other tumors, is why polypeptides such as EMAP I, VPF/VEGF, and EMAP II do not result in a more striking host response in the tumor bed. On the one hand, other components of the tumor milieu, such as binding proteins, proteases or cytokines with opposing actions, could modulate their effects. Alternatively, the amount of EMAP II or other mediators elaborated by tumors in vivo might be insufficient to induce an optimal host response. Future studies, employing neutralizing antibodies to these polypeptides and cell lines expressing variable amounts of these mediators, will be required to directly assess the effect of tumor-derived cytokines on the neoplasm.

B. PEPTIDE DERIVED FROM THE AMINO TERMINUS OF ENDOTHELIAL-MONOCYTE ACTIVATING POLYPEPTIDE II

MATERIALS AND METHODS

Purification of EMAP II, preparation and radiolabelling of synthetic peptides. Murine EMAP II (EMAP II), purified as described (7), was homogeneous on SDS-PAGE, migrating as single band, Mr ≈18 kDa. Elution of the latter band from SDS-PAGE demonstrated its capacity to induce EC and MP tissue factor activity, as well as to promote MP and PMN migration, as described previously (7). A series of peptides were prepared based on the N-terminal sequence of murine EMAP II (7) via solid phase methodology (22) using either t-boc or f-moc chemistry. Crude peptides were purified by HPLC and analyzed via mass spectrometry. The peptide RIGRIIT was generously provided by Drs. Arun Patel and George Glover (SmithKline Beecham, King of Prussia Pa.). As indicated, peptides were prepared with an additional C-terminal tyrosine to facilitate radioiodination by the chloramine T method (23). The final specific radioactivity of RIGRIVTAKY was $3 \times 10^5$ cpm/ng.

Murine tumor necrosis factor-α(TNF) was purchased from Genzyme (Cambridge Mass.), murine IL-1α (TNF) was generously provided by Dr. Peter Lomedico (Hoffmann-LaRoche, Nutley N.J.), and formyl-methionyl-leucinyl-phenylalanine (fMLP) was obtained from Sigma (St. Louis Mo.).

Preparation of PMNs, MPs, and ECs. Human PMNs were isolated from heparinized blood of normal volunteers by centrifugation over HISTOPAQUE 1119 (Sigma). Pellets containing erythrocytes and PMNs were diluted 1:2 in normal saline, exposed to NaCl (0.2%) for 20 sec (to lyse erythrocytes), restored to isotonicity, and centrifuged (350× g) for 10 min (7,24). The latter procedure was repeated twice, and the resulting cell population, >98% PMNs, was resuspended in RPMI 1640 containing heat-inactivated human serum (5%; Gemini, Calabasas Calif.) at a density of ≈$10^8$ cells/ml. Human peripheral blood monocytes were isolated by centrifugation on HISTOPAQUE 1077 (Sigma). The mononuclear fraction was obtained, washed twice in Hank's balanced salt solution, resuspended in RPMI 1640 containing human serum (10%), and subjected to an adherence step on tissue culture plasticware. The adherent cell population was harvested by incubation in calcium-magnesium-free buffer containing EDTA, as described previously (7,25), and MPs were resuspended in RPMI 1640 containing human serum (10%) at a density of $10^6$ cells/ml. Human umbilical vein ECs were prepared by the method of Jaffe (26) as modified by Thornton et al (27, and were characterized as described previously (28). Experiments were carried out within 48 hrs of the cells achieving confluence.

Assays of MP, PMN, and EC properties. The effect of synthetic peptides on MP and PMN migration and cytosolic $[Ca^{2+}]_i$, MP and EC tissue factor, and PMN peroxidase release was studied as described below.

Cell migration was studied by adding MPs or PMNs ($10^4$ cells/well) resuspended in RPMI 1640 with fetal calf serum (1%; Gemini) to the upper wells of a microchemotaxis chamber (Neuro Probe, Bethesda, Md.) containing Nucleopore polycarbonate membranes (5 µm, Nucleopore, Pleasanton Calif.), as described (7,29–30). The chemotactic stimulus was placed in the upper or lower chamber, as indicated, and cells were allowed to migrate for 3 hrs (for MPs) or 45 min (for PMNs) at 37° C. Following removal of non-migrating cells, membranes were fixed in methanol and migrating cells were visualized with Wright's stain. Assays were performed in quadruplicate, and cells were counted in nine high-power fields in each case (mean ±SEM is shown in the figures).

Tissue factor activity of monolayers of ECs and MPs was determined (7) after incubation with EMAP II-derived peptides at 37° C. for 4–12 hrs by washing cultures with HEPES (10 mM; pH 7.4), NaCl (137 mM), KCl (4 mM), $CaCl_2$ (3 mM), glucose (10 mM), bovine serum albumin (0.5 mg/ml), and addition of 0.5 ml of the same buffer along with purified human Factor VIIa (1 nM) and Factor X (200 nM) for 45 min at 37° C. Aliquots (0.05 ml) of the reaction mixture (one per well) were withdrawn at 15 min intervals, added to a buffer containing Tris (50 mM; pH 7.9), NaCl (175 mM), EDTA (5mM) and bovine serum albumin (0.5 mg/ml; 0.05 ml), and the chromogenic substrate Spectrozyme Factor Xa (American Diagnositca, Inc., Greenwich Conn.; 0.01 ml; 2 mM). Cleavage of the substrate was monitored by the change in absorbance at 405 nm (BioKinetics Reader, Winooski, Vt.). Factor Xa concentration was determined by comparison with a standard curve generated with known amounts of purified human Factor Xa. Human, plasma-derived Factors VIIa and X were purified to homogeneity as described (31).

$[Ca^{2+}]_i$ measurements. PMNs or MPs ($2 \times 10^7$ cells in each case) were incubated with fura-2AM (1 µM) and pluronic detergent (0.02%) for 12 min at room temperature, diluted sixfold, and incubated for a further 30 min at room temperature to allow for complete hydrolysis of the dye. Cells were then resuspended in HEPES-buffered saline at $5 \times 10^5$ cells/ml (32). For experiments using MPs, sulfinpyrazone (0.5 mM) was included at all steps to minimize both dye sequestration into intracellular organelles and dye efflux (33). Fluorescence of fura-2 was monitored at 37° C. in a thermostatically-controlled cuvette installed in a Perkin Elmer Model 650-40 fluorescense spectrophotometer. Calibration of $[Ca^{2+}]_i$ was performed as described (34).

Release of peroxidase generating activity from PMNs (myeloperoxidase) was determined by oxidation of the peroxidase substrate 3,3',5,5'-tetramethylbenzidine (TMB; Sigma), monitored at 620 nm, as described (35). In brief, PMNs ($3 \times 10^6$ cells/ml; 0.05 ml) were incubated for 60 min at 37° C. with RPMI 1640 containing fetal calf serum (1%) alone or in the presence of phorbol ester (phorbol 12-myristate 13-acetate; Sigma) or EMAP II-derived peptides. TMP and hydrogen peroxide were added for 1 min at room temperature, and the reaction was stopped with sodium azide and acetic acid. Peroxidase activity, assessed by oxidation of TMB, was determined spectrophotometrically and is reported as percent total peroxidase activity (100% is the activity observed with that number of PMNs following 60 min exposure to phorbol ester, 10 µM). A standard curve was generated by assaying peroxidase activity from different numbers of PMNs treated with phorbol ester (10 µM) under these conditions, and peroxidase activity of PMN/EMAP II peptide incubation mixtures was determined by comparison with the linear portion of the standard curve (35).

Cell binding and cross linking studies.

Radioligand binding studies were performed on human MPs plated in 96-well plates ($5-6 \times 10^4$ cells/well). Cells were washed twice with Hanks balanced salt solution, and then Dulbecco's Modified Eagle Medium containing HEPES (25 mM; pH 7.4), penicillin/streptomycin (50 U/ml; 50 µg/ml), and bovine serum albumin-fatty acid free (0.5%; Sigma) were added (0.1 ml/well). Cultures were incubated at 4° C. for 2 hrs with $^{125}$I-RIGRIVTAKY alone or in the presence of unlabelled peptide/protein. Each well was washed four times over a period of 20 sec, and cell-associated radioactivity was eluted by an acidic buffer (HCl, 0.1 M, pH 2; NaCl, 0.1M) at 4° C. for 5 min. During the elution period, there was no detachment of cells from the growth substrate. The conditions for incubation and washing used in the binding studies shown in FIGS. 3A–3D (2 hrs at 4° C.) were insufficient to allow binding of $^{125}$I-RIGRIVTAKY to reach an apparent maximum, even at the lowest tracer concentrations, and to remove unbound material by washing quickly so that <10% of the cell-bound radioactivity dissociated. Binding data were analyzed according to the equation of Klotz and Hunston (36), B=nKA/(1+KA), where B=specifically bound ligand (specific binding=total binding, wells incubated with tracer alone, minus nonspecific binding, wells incubated with tracer in the presence of excess unlabelled material), n=sites/cell, K=the dissociation constant, and A=free ligand concentration using nonlinear least-squares analysis (Enzfitter, Cambridge UK).

Cross-linking experiments were performed on MPs plated in 24-well plates ($1.5-2.5 \times 10^5$ cells/well) and incubated with radiolabelled peptides as described above. At the end of the incubation period, disuccinimidyl suberate (0.2 mM; Pierce, Rockford, Ill.)(37) was added for 15 min at room temperature. Cultures were then washed four times with Hanks balanced salt solution, solubilized with lysis buffer (Tris, 10 mM, pH 7.5; NP-40, 1%; EDTA, 1 mM; PMSF, 1 mM; pepstatin A, 1 µg/ml; aprotinin, 1.5 µg/ml) and centrifuged (13,000×g for 10 min) to remove cellular debris. Proteins that remained in the supernatants were precipitated by trichloroacetic acid (20%, final concentration). The pellet was washed twice with ice-cold acetone, dried (SpeedVac, Savant, Farmingdale, N.Y.), solubilized and prepared for non-reduced SDS-PAGE (4–15%, Bio-Rad, Hercules Calif.) (38). After electrophoresis, gels were dried and subjected to autoradiography. The approximate Mr of the band corresponding to putative complexes of $^{125}$I-RIGRIVTAKY-cell surface proteins was estimated based on the migration of simultaneously run standard proteins (Amersham, Arlington Heights, Ill.): myosin (200 kDa), phosphorylase b (97.4 kDa), bovine serum albumin (69 kDa), ovalbumin (46 kDa), carbonic anhydrase (30 kDa) trypsin inhibitor (21.5 kDa), and lysozyme (14.3 kDa). Preparation and implantation of peptide-albumin conjugates into mice. Peptide-albumin conjugates (made with either ASRLDLRIGRIVTAKY (SEQ ID NO: 6, RIGRIVTAKY (SEQ ID NO: 4) or CRAQTMANSGIK (SEQ ID NO: 16) were prepared using glutaraldehyde as described (39). In brief, mouse serum albumin (50 µg) was incubated with glutaraldehyde (450 µg) and the indicated peptide (200 µg) in NaCl (0.1M) Tris (0.05M; pH 7.3) for 10 min at room temperature. Excess lysine was added (final concentration, 0.5M), and the albumin-peptide conjugates were dialyzed exhaustively versus phosphate-buffered saline. BALB/c mice (6–12 weeks) each received an injection into the footpad (7,40–41) of 0.05 ml of a solution of either (i) albumin-peptide conjugate (50 µg, total protein/footpad), (ii) albumin treated with glutaraldehyde in an identical fashion, except that no peptide was present (50 µg, total protein/footpad), (iii) native albumin (50 µg total protein/footpad), or (iv) buffer alone. At the indicated time, animals were sacrificed by humane euthanasia, footpads were harvested, fixed in buffered formalin (10%), decalcified, and embedded in paraffin. Sections were stained with hematoxylin and eosin.

RESULTS

Effect of N-terminal derived EMAP II peptides on PMNs and MPs. In view of the close homology between a short span of EMAP II (residues #10–20)(7) and von Willebrand factor antigen II (residues #480–490)(14–15), and the similar cytokine-like properties of these molecules (18), a peptide homologous to the N-terminal region of murine EMAP II was prepared and its effects on PMNs and MPs were tested. Since the peptide including residues #6–20 from EMAP II, ASRLDLRIGCIVTAK (SEQ ID NO: 5), proved to be unstable/insoluble, the Cys residue (residue #15) was replaced with an Arg, similar to that present in the comparable position (residue #485) in vonWillebrand antigen II (14–15). Incubation of PMNs with ASRLDLRIGRIVTAKY (SEQ ID NO: 6) (residues #6–20 from EMAP II, Cys to Arg substitution at position #15, and a C-terminal Tyr) led to induction of migration, compared with controls containing medium alone. In contrast, no chemotaxis was observed with a peptide derived from the C-terminal portion of EMAP II (CRAQTMANSGIK (SEQ ID NO: 16)), a peptide derived from the ELR-region of IL-8 (AVLPRSAKELRL (SEQ ID NO: 17); residues #23–34) (42–43), or an irrelevant peptide derived from growth hormone (IRKDMDKVETFLRIVQ (SEQ ID NO: 18)). Induction of PMN migration by ASRLDLRIGRIVTAKY (SEQ ID NO: 6) at 100 pM was roughly comparable to that observed with formulated chemotactic peptide fMLP (44) at 1 µM. The effect of ASRLDRIGRIVTAKY (SEQ ID NO: 6) added to the lower well of chemotaxis chambers was dose-dependent over a range of 10–10000 pM, and at doses >1 nM reached an apparent maximum (data not shown). In four different experiments using PMNs from three individuals and multiple concentrations of peptide, half-maximal PMN migration occurred at an ASRLDLRIGRIVTAKY (SEQ ID NO: 6) concentration of ≈150–300 pM. The peptide induced directional PMN migration rather than simply chemokinesis since addition of peptide to the upper well attenuated/abolished the response to ASRLDLRIGRIVTAKY (SEQ ID NO: 6) added to the lower well. In addition to stimulating PMN motility, ASRLDLRIGRIVTAKY (SEQ ID NO: 6) also released PMN myeloperoxidase activity in the peroxidase generation assay, as did phorbol ester-treated positive controls. In contrast, negative controls utilizing the EMAP II C-terminal peptide (CRAQTMANSGIK (SEQ ID NO: 16)) or medium alone demonstrated no induction of cell migration.

To further elucidate structural determinants in the N-terminal region of EMAP II (residues #6–20) critical for induction of PMN migration, a series of synthetic peptides was prepared (Table 4).

TABLE 4

Effect of peptides derived from the N-terminus of EMAP II on PMN migration@

| PEPTIDE | PMN MIGRATION |
| --- | --- |
| 1. A S R L D L R I G R I V T A K Y (SEQ. ID NO: 6)# | + |
| 2. A S R L D L R I G R I V T A K (SEQ. ID NO: 7) | + |
| 3. A S R L D L R I G C*I V T A K (SEQ. ID NO: 5) | + |
| 4. A S R L D L (SEQ. ID NO: 19) | − |
| 5.             L R I G R I V T A K Y (SEQ. ID NO: 8) | + |
| 6.                 R I G R I V T A K Y (SEQ. ID NO: 6) | + |
| 7.                 R I G R I V T (SEQ. ID NO: 5) | + |
| 8.                 R I G R I I T (SEQ. ID NO: 9) | + |
| 9.                 R I G R A V T (SEQ. ID NO: 20) | − |
| 10.                    A I G R I V T (SEQ. ID NO: 10) | + |

@cell migration assays were performed using PMNs and peptides (100 pM in each case) as described in the text. (+) indicates the peptide induced PMN migration. (−) indicates the peptide did not induce PMN migration above levels seen in controls which contained no chemotactic stimulus. Each experiment was repeated at least three times.
Residues of peptides were assigned numbers (referred to in the text) starting with #6, N-terminal A, to #21, C-terminal Y. These numbers were based on the N-terminal protein sequence of EMAP II in which A was residue #6.
*Cys at this position was carboxymethylated.

For these studies, comparable molar concentration of peptide were employed, and where the data is reported as (+), there was a similar response (the designation [−] indicated no response above that observed in untreated control wells). The data is reported in this nonquantitative fashion because absolute numbers migrating cells vary in different assays (PMNs from different donors, assays performed on different days), though the same trend was observed over a similar range of peptide concentrations. Compared with ASRLDLRIGRIVTAKY (SEQ ID NO: 6) (line 1), the peptide ASRLDLRIGRIVTAK (SEQ ID NO: 7) without an added C-terminal Tyr residue promoted PMN Migration (line 2). Since we had arbitrarily replaced Cys (residue #15 in EMAP II) with Arg to enhance peptide stability, it was important to determine if this substitution, which also made the peptide more positively charged, altered its biologic properties. A peptide in which the Arg at position #15 in the peptide was replaced with carboxymethylated-Cys (line 3) was prepared and found to induce PMN migration. To determine which portion of the sixteen residue peptide was involved in the interaction with PMNs, we synthesized several shorter peptides. ASRLDL (SEQ ID NO: 19) (residues #6–11; line 4), the N-terminal region of the initial peptide #6–20), was inactive in the PMN migration assay, whereas several peptides closer to C-terminus were active: LRIGRIVTAKY (SEQ ID NO: 8) (#11–20; line 5), RIGRIVTAKY (SEQ ID NO: 6) (#12–20; line 6), and RIGRIVT (SEQ ID NO: 3) (#12–18; line 7). Our recent molecular cloning studies have shown that, in the human homologue of EMAP II, Val at position #17 in murine EMAP II is replaced by Ile; thus, the latter peptide was tested (RIGRIIT (SEQ ID NO: 9); resides #12–18; line 8) and was found to stimulate PMN migration. Whereas replacement of Ile (position #16) with Ala in this peptide rendered it inactive (RIGRAVT (SEQ ID NO: 20); line 9), substitution of Arg at position #12 with Ala (AIGRIVT, (SEQ ID NO: 10) resides #12–18; line 10) resulted in a peptide which retained activity for induction of PMN migration.

When the same peptides employed in the studies with PMNs were studied for their effects on MP migration, ASRLDLRIGRIVTAKY (SEQ ID NO: 6) was found to induce chemotaxis, whereas the C-terminal EMAP II-derived peptide, as well as the IL-8-derived peptide and growth hormone-derived peptide were inactive, i.e., comparable to medium alone. Migration of MPs in the presence of ASRLDLRIGRIVTAKY (SEQ ID NO: 6) at a concentration of 100 pM was similar to that observed with FMLP at 1 µM. The effect of ASRLDLRIGRIVTAKY (SEQ ID NO: 6) on MP migration was dependent on the amount of peptide added to the lower compartment of the microchemotaxis chamber over a similar concentration range to that observed with PMNs and the effect was prevented by addition of peptide to the upper compartment of the chamber.

In view of the similar effects of the N-terminal EMAP II-derived peptides and intact EMAP II for the induction of MP and PMN chemotaxis, experiments were performed to determine if peptides mimicked other activities of EMAP II (7). However, studies with ECs and MPs did not demonstrate induction of tissue factor activity by any of the peptides from EMAP II, based on Factor VIIa-dependent Factor X activation, when either of these cell types was incubated with a range of ASRLDLRIGRIVTAKY (SEQ ID NO: 6) concentrations. In contrast, intact EMAP II stimulated tissue factor expression in ECs and MPs (7).

Binding and cross-linking of $^{125}$I-EMAP II-derived N-terminal region peptide to MPs. To delineate further the interaction of EMAP II-derived peptides with target cells, the tyrosinated derivative of RIGRIVTAKY (SEQ ID NO: 4) was radioiodinated and employed as a tracer for binding studies. Incubation of $^{125}$I-RIGRIVTAKY (SEQ ID NO: 21) with MPs led to dose-dependent specific binding at 4° C. Binding data fit a one-site model with Kd=0.19±0.11 nM and N=8.3±1.2×$10^3$ molecules of peptide bound per cell. Competitive binding studies demonstrated inhibition of $^{125}$I-RIGRIVTAKY (SEQ ID NO: 21) binding in the presence of increasing concentrations of unlabelled RIGRIVTAK (SEQ ID NO: 2) and ASRLDLRIGRIVTAKY (SEQ ID NO: 6). CRAQTMANSGIK (SEQ ID NO: 16), derived from the C-terminal region of EMAP II, ASRLDL (SEQ ID No: 19), derived from the first six amino acids of the original peptide (residues #6–20), and RIGRAVT (SEQ ID NO: 20) had no effect. These data are consistent with the lack of effect on PMN chemotaxis of ASRLDL (SEQ ID NO: 19) (line 4, Table 4), RIGRAVT (SEQ ID NO: 20) (line 9, Table 4) and CRAQTMANSGIK (SEQ ID NO: 16). Further evidence for the specificity of $^{125}$I-RIGRIVTAKY (SEQ ID NO: 21) interaction with cellular surfaces was based on inhibition of binding on addition of excess unlabelled intact EMAP II, but not by fMLP, murine TNFα or murine Il-1α.

In order to better define MP cell surface structures with which $^{125}$I-EMAP II interacted, cross-linking studies with DSS were performed. Addition of cross-linker to MPs with cell-bound $^{125}$I-RIGRIVTAKY (SEQ ID NO: 21) resulted in the appearance of a ≈73 kDa band on autoradiograms of reduced SDS-Page. The likelihood that the latter ≈73 kDa band was due to a MP polypeptide potentially contiguous to cell-bound $^{125}$I-RIGRIVTAKY (SEQ ID NO: 21) was supported by the results of experiments demonstrating disappearance/striking reduction of the ≈73 kDa band when: (i) DSS was added to $^{125}$I-RIGRIVTAKY (SEQ ID NO: 21) alone (i.e., MPs were omitted); (ii) DSS was omitted from incubation mixtures containing $^{125}$I-RIGRIVTAKY (SEQ ID NO: 21) and MPs; (iii) excess unlabelled RIGRIVTAKY (SEQ ID NO: 21) was added to reaction mixtures containing $^{125}$I-RIGRIVTAKY (SEQ ID NO: 21) and MPs, and cross-linked with DSS.

EMAP II-derived N-terminal peptide increases [Ca$^{2+}$]$_i$ in MPs and PMNs. ASRLDLRIGRIVTAKY (SEQ ID NO: 6) induced a rise in [Ca$^{2+}$]$_i$ in PMNs, similar to results using the intact EMAP II molecule. The rise in [Ca$^{2+}$]$_i$ was due mainly to redistribution of Ca$^{2+}$ from intracellular stores since a similar increase was seen when the cells were incubated in Ca$^{2+}$-free medium containing 5 mM EGTA. Neither the shorter peptides RIGRIVT (SEQ ID NO: 3) nor RIGRIVTAKY (SEQ ID NO: 4) were capable of inducing a rise in [Ca$^{2+}$]$_i$ in PMNs when used at the same concentration, and the hexapeptide ASRLDL, derived from the N-terminus of the larger peptide, was also inactive in this regard. Similar results were seen in MPs, except the magnitude of rise in [Ca$^{2+}$]$_i$ from peptide stimulation was less than that of PMNs. These observations indicate that ASRLDLRIGRIVTAKY (SEQ ID NO: 6), derived from the N-terminus of EMAP II, results in elevation of [Ca$^{2+}$]$_i$ in PMNs and MPs, but that a rise in [Ca$^{2+}$]$_i$ is not necessary for migration per se since the shorter migration-inducing peptides did not promote enhanced [Ca$^{2+}$]$_i$.

Implantation of EMAPII-derived peptide-albumin conjugates into mice. To complement in vitro studies, experiments were performed in vivo to determine if the peptide had the ability to incite an inflammatory response. The mouse footpad was selected as a model system for these experiments since it is well-characterized and provides a relatively confined space for testing the host response to inflammatory cytokines, such as intact EMAP II as will as other mediators (7,40–41). Initial experiments employing ASRLDLRIGRIVTAKY (SEQ ID NO: 6) injected subcutaneously into mice demonstrated at most a transient inflammatory response, probably due to rapid diffusion of the small peptide away from the implantation site. For this reason, ASRLDLRIGRIVTAKY (SEQ ID NO: 6) and RIGRIVTAKY (SEQ ID NO: 4) were conjugated to albumin using glutaraldehyde, and the experiments were repeated. First, we verified the chemotactic activity of peptide-albumin conjugates in vitro with MPs and PMNs; ASRLDLRIGRIVTAKY(SEQ ID NO: 6)-albumin induced both MP and PMN migration compared with medium alone. In contract, neither albumin treated with glutaraldehyde nor albumin alone induced migration. In other experiments, RIGRIVTAKY(SEQ ID NO: 4)-albumin conjugates were shown to have chemoattractant properties for PMNs and MPs, whereas CRAQTMANSGIK(SEQ ID NO: 16)-albumin did not. When ASRLDLRIGRIVTAKY(SEQ ID NO: 6)-albumin or RIGRIVTAKY(SEQ ID NO: 4)-albumin was injected into mouse footpads, tissue infiltration with inflammatory cells, especially PMNs, was observed (shown at 6 hr in FIGS. 3A–3D), whereas the same amount of albumin or glutaraldehyde-treated albumin was without effect. In contrast, footpads injected with CRAQTMANSGIK(SEQ ID NO: 16)-albumin were indistinguishable from untreated controls.

DISCUSSION

EMAP II, a novel polypeptide mediator made by the immunogenic murine meth A fibrosarcoma, modulates cellular properties resulting in induction of tissue factor in ECs, in tissue factor and cell migration in MPs, and in cell migration and release of myeloperoxidase in PMNs (7 and unpublished observation). Based on the activities of EMAP II in vitro, and its ability to induce an acute inflammatory response in vivo (7), it was hypothesized that it may contribute to the host response elicited by immunogenic tumors (1–4). To define regions of EMAP II which are recognized by putative receptors on target cells, it is demonstrated that synthetic peptides comprising fifteen amino acids near the N-terminus of murine EMAP II (residues #6–20) promote PMN and MP migration, elevate $[Ca^{2+}]_i$, and lead to release of PMN peroxidase activity. These data, in addition to the demonstration that albumin conjugates of EMAP II-derived N-terminal peptides lead to an inflammatory infiltrate when injected into mouse footpads, support the concept that this peptide comprises a functional domain of EMAP II.

Our first structure-function studies of the peptide demonstrated that although ASRLDLRIGRIVTAKY (SEQ ID NO: 6) stimulated both chemotaxis and increase cytosolic calcium in MPs and PMNs, the shorter peptide RIGRIVT (SEQ ID NO: 3) was sufficient to stimulate chemotaxis, but insufficient to promote increases in $[Ca^{2+}]_i$. Thus, RIGRIVT (SEQ ID NO: 3) is an example of a stimulus which promotes cell migration without altering cytosolic calcium, as had been observed with tumor necrosis factor-α (45 and S. Greenberg, unpublished observation). This suggests that the longer peptide, ASRLDLRIGRIVTAKY (SE ID NO: 6), might have two functional domains, whereas the shorter peptide, RIGRIVT (SEQ ID NO: 3), had more limited activity. In view of the lack of calcium mobilizing activity of ASRLDL (SEQ ID NO: 19), we hypothesize that attachment of these residues to RIGRIVTAK (SEQ ID NO: 22) is required for cellular association and subsequent stimulation of $[Ca^{2+}]_i$. The results of radioligand binding studies on MPs supported this view, since binding of $^{125}$I-RIGRIVTAKY (SEQ ID NO: 21) to cells was blocked by excess unlabelled RIGRIVT (SEQ ID NO: 3) and ASRLDLRIGRIVT (SEQ ID NO: 23), but not ASRLDL (SEQ ID NO: 19). Analysis of residues within the septa-peptide RIGRIVT (SEQ ID NO: 3) that contribute to induction of PMN migration has demonstrated the importance of the sequence XIGXI(V/I)T (SEQ ID NO: 24), (SEQ ID NO: 25), although further studies will be necessary to precisely determine structure-function relationships.

Experiments with $^{125}$I-RIGRIVTAKY (SEQ ID NO: 21) demonstrated specific and saturable binding to human MPs. Pilot studies using ECs also show specific binding of this peptide (data not shown). Competition studies in which neither murine TNFα, IL-1α, nor fMLP inhibited binding of $^{125}$I-RIGRIVTAKY (SEQ ID NO: 21) to MPs suggested that cell surface acceptor sites interact specifically with EMAP II-related ligands. Consistent with the potential selectivity of EMAP II-derived peptide-cell surface interaction, cross-linking studies with $^{125}$I-RIGRIVTAKY (SEQ ID NO: 21) labelled and ≈73 kDa MP surface polypeptide. The potential uniqueness of the cellular recognition site for the N-terminal region of EMAP II was also suggested by our recent molecular cloning studies which have shown that its ligand, EMAP II, is novel, and is not, on the basis of primary structure, a member of either a known cytokine (such as IL-1 or TNF)(46–47) or chemokine (IL-8 and related murine homologs)(48) family.

Taken together, these data provide a starting point for more detailed structure-function studies of EMAP II, and highlight contributions of an N-terminal functional domain for modulation of MP and PMN properties. However, it is important to note that none of the peptides studied fully mimicked the cellular effects of intact EMAP II. For example, even the longest peptide (residues #6–20) did not induce tissue factor in ECs or MPs. Thus, there are likely to be several functional domains which account for EMAP II-induced modulation of cellular functions. In this context, the design of peptide agonists and antagonists of the N-terminal region may provide valuable reagents for analyzing cellular effects of EMAP II and isolating the putative cell surface receptor.

C. cDNA CLONE AND RECOMBINANT EMAP II

MATERIALS AND METHODS

Isolation of Meth A cell RNA. Meth A cells were grown in RPMI 1640 containing fetal bovine serum (10%; Hyclone, Sterile Systems, Logan, Utah) to ≈90% confluence, cells were harvested (≈$10^8$) with trypsin, resuspended in fetal bovine serum (10%), and poly(A)$^+$RNA isolated directly as described (Bradley 1988). Briefly, cells were lysed in SDS-containing buffer and proteins were digested with proteinase K (Boehringer Mannheim, Indianapolis, Id.) for 3 hr at 55° C. Oligo(dt)cellulose (Collaborative Biomedical, Bedford, Mass.) was added and the poly(A)$^+$RNA removed by centrifugation and then eluted with water. A second step in the purification utilized oligo (dt) cellulose bound to magnetic beads (Promega, locationx) by a similar procedure.

Isolation of murine cDNA clones. Meth A mRNA (1 µg) was denatured with MeHgOH and reverse transcribed with AMV reverse transcriptase using oligo(dt)$_{17}$ as a primer. The first strand cDNA obtained was used as template for the polymerase chain reaction (PCR) using degenerate primers based on the amino terminal protein sequence obtained for EMAPII. The sense primer was 5'-AARCCNATHGAYGC (SEQ ID NO: 26)-3' and the antisense primer was 5'-YTTNGCNGTNACDAT (SEQ ID NO: 27)-3', 48- and 184-fold degenerate, respectively. In addition, both primers contained EcoRI sites to facilitate cloning of the PCR products. The thermocyte parameters consisted of three cycles of 95° C. for 30 sec, one min to reach 37° C., 30 sec at 37° C., 2.5 min to 72° C., one min at 72° C., and one min to reach 95° This was followed by 30 cycles of 30 sec at 95° C., 30 sec at 55° C., and one min at 72° C. Analysis of the amplified products on an acrylamide gel showed a DNA fragment of the expected size of 77 bp. The PCR products were then digested with EcoRI, run on an acrylamide gel, the appropriate band excised and eluted, and the DNA fragment cloned into the plasmid vector pUC219. Plasmids containing EcoRI inserts were sequenced by the Sanger dideoxynucleotide method using Sequenase (US Biochmical Corp.). The deduced amino acid sequence was found to match exactly that obtained by protein sequencing. A 57-mer nucleotide probe was designed based on the consensus nucleotide sequence obtained from sequencing several clones (5'-AAGCCCATTGATGCCTCCCGGCTGGAC- CTGCGGATTGGCTGCATTGTGACAGC CAAG (SEQ ID NO: 28)-3'). This probe was end-labelled with [τ$^{32}$P] dCTP using polynucleotide kinase and employed to screen a Meth A cDNA library in the lambda vector HEBO5 (Leung et al, 1992). Hybridization was in formamide (20%), SSC (5x), sodium phosphate (50 mM; pH 6.5), denatured salmon sperm DNA (40 µg/ml), SDS (0.1%), and Denhardt's solution (5x) at 42° C. One positive plaque was identified which contained a 700 bp insert. A second library, in lambda-gt10, was constructed from cDNA primed with a specific primer, 5'-ATTTTGCATCTGTTCTAG- (SEQ ID NO: 29) -3', complementary to sequence near the 5'-end of the original clone. This library was screened with the same oligonucleotide probe described above under the same conditions. Eight positive plaques were obtained from ≈$10^5$ screened. The three with the longest inserts, all ≈300 bp, were subcloned into the EcoRI site of pUC219 and sequenced. When this sequence was overlapped with the original clone, an 1086 bp sequence was obtained. A full length EMAPII cDNA was constructed in the Epstein-Barr virus-based vector, pHEB023 (Leung et al, 1992), by joining the two fragments at the XbaI restriction site present in both pieces.

Cloning of the Human EMAPII cDNA. Low strigency Northern analysis of human U937 mRNA using a murine probe suggested the EMAPII transcript was expressed by this cell line (data not shown). Thus, an oligo(dt)-primed U937 library in lambda-gt10 (kindly provided by Brain Bennet, Genetech, So. San Francisco, Calif.) was screened. Plaques (≈$10^6$) were screened using a probe consisting of the first 310 nucleotides at the 5'-end of the murine EMAP II clone. This ClaI (in the vector polylinker) to ScaI (500 bp) fragment ws nick-translated and hybridized in formamide (20%), sodium phosphate (50 mM; pH 6.5), SSC (5x), Denhardt's solution (5x), SDS (0.1%), and denatured salmon sperm DNA (40 µg/ml) at 42° C. About 20 positives were obtained, and ten of these were purified. The three which contained the longest inserts appeared to have identical 1100 bp EcoRI inserts. These inserts were subcloned in pUC219 and sequenced.

Northern analysis of Meth A cell mRNA for EMAPII expression. Poly(A)+RNA from MethA sarcoma cells was denatured and electrophoresed on an agarose gel (1.2%) in MOPS-formaldehyde (Sambrook et al, 1989). The RNA was transferred to nitrocellulose (Schleicher and Schuell) and prehybridized in formamide (50%), sodium phosphate (50 mM; pH 6.5), SSC (5x), Denhardt's solution (5x), SDS (0.1%), and denatured salmon sperm DNA (40 µg/ml) at 42° C. A 279 bp DNA fragment was isolated from the murine EMAPII clone following XbaI and SacI digestion corresponding to nucleotides 652–930. This was nick-translated with [α$^{32}$P]dCTP and hybridized to the blot overnight. Washing was performed at a final stringency of SSC (0.2x) /SDS (0.1%) at 55° C. The blot was then exposed overnight for autoradiography.

E. coli expression of murine EMAPII. In order to confirm the biological activity of the protein encoded by the cloned DNA sequence, the region corresponding to the predicted mature protein, based on the N-terminal sequence obtained from purified EMAPII, was expressed. This was accomplished using a fragment of the murine clone extending from the BstB I site (nucleotide 529) to the 3'-untranslated region and synthetic DNA encoding the N-terminal end, KPIDAS-RLEL (SEQ ID NO: 30) (5'TATGAAACCAATCGATGCAT CTCGTCTGGATCTT (SEQ ID NO: 31)-3' AND 5'-CGAAGATCCAGACGAGATGCATCGATTGGTTTCA (SEQ ID NO: 32-3'). This sequence, which differs from the amino terminal region obtained by microsequencing because the N-terminal residue, serine, was inadvertently omitted when designing the synthetic DNA, was cloned into the NdeI site, containing the ATG initiation codon, and the BamHI site of the vector pET-3a in which cDNA expression is driven by the T7 promoter (novagen). The protein was then expressed in the host HMS174(DE3) which contains the T7 RNA polymerase gene under control of the lacUV5 promoter. Following growth to log phase the T7 polymerase was induced with IPTG (0.4 mM) and the cells were harvested by centrifugation 3 hr later.

Transfection of Meth A cells. Meth A cells, a methylcholanthrene A-induced fibrosarcoma originally derived from BALB/c mice were generously provided by Dr. L. Old (Ludwig Cancer Inst., NY). Cells were grown in RPMI 1640 (Gibco BRL, Grand Island, N.Y.) containing fetal calf serum (10%; HyClone Laboratories, Logan, Utah) penicillin/streptomycin (1x; Gibco BRL), and L-glutamine (2mM) (this is termed complete medium-CRPMI), and maintained at 37° C. in a humidified, 5% $CO_2$ atmosphere. The medium for selection of transfectants contained G418 (400 µg/ml; Gibco BRL). Full-length EMAP II cDNA was subcloned into the pRK5 plasmid. Exponentially growing Meth A cells were transfected with Cel-Porator electroporation System I (Gibo BRL). Briefly, serum-free RPMI (1 ml) containing meth A cells (2x$10^6$), pRK5-proEMAPII cDNA (20 µg), and pRK5-Neo DNA (1 µg; containing the G418 resistence gene) was transferred into the electorporation chamber, and the electorporation ws conducted at 250 V. After transfection, the cells were incubated for 15 min at 23° C., and then transferred to CRPMI (15 ml). After a further 24 hrs, cells were pelleted, resuspended in the selective medium containing G418 (400 µg/ml), and aliquoted into four 48-well plates. Cells were re-fed with selective medium every three days, and 2–3 weeks later colonies became visible. Wells with a single colony were chosen for expansion. Production of EMAPII antigen was quantitated by ELISA.

Preparation of and in vitro assays with endothelial cells, mononuclear phagocytes (MPs), polymorphonuclear leukocytes (PMNs). Human umbilical vein ECs were prepared by the method of Jaffee et al as modified by Thornton et al, as done previously (7). Bovine aortic ECs were harvested fron the aortae of veal calves and grown in culture as described previously. Human peripheral blood monocytes were isloated from the blood of normal healthy volunteers. Blood was centrifuged on Histopaque 1077 (Sigma), the mononuclear fraction was obtained, washed twice in Earle's balanced salt solution, resuspended in RPMI 1640 containing human serum (10%, Gemini, Calabases, Calif.), plated on tissue culture dishes, and incubated at 37° C. for 1–2 h. Nonadherent cells were removed by washing the plate twice with balanced salt solution, and adherent cells were harvested by incubation with calcium-magnesium free buffer containing EDTA (2 mM) for 15 min at 37° C., followed by extensive washing. PMNs were prepared by centrifugation over HISTOPAQUE 1119 according to the manufacturer's protocol (Sigma).

RESULTS cDNA cloning of EMAPII. Purification of EMAPII from conditioned medium of murine meth A sarcoma yielded an ≈22 kDa protein from which an unique amino terminal sequence was obtained. Degenerate oligonucleotide primers were designed to generate a 77 bp fragment encoding a portion of the N-terminal sequence by PCR. The sequence obtained was then used as the basis for design of a 57 base oligonucleotide probe for screening a meth A oligo(dt)-primed cDNA library. One clone, 680 bp, was isolated and represented a partial cDNA sequence with an open reading frame at the 5'-end. A second meth A cDNA library was constructed using a specific primer based on the first sequence obtained, and the same 57 base probe was used to identify 8 clones. Three of these appeard to have identical inserts of 660 bp based on restriction analysis, and the sequence obtained from these clones was overlapped with that of the original clone to produce contiguous sequence of 1086 bp (FIGS. 4A–4D). Northern blot analysis of RNA from Meth A cells using a 275 bp XbaI to SacI fragment as a probe demonstrated a single transcript of approximately 1070 bp suggesting the cDNA clone was full-length. Analysis of this sequence revealed an open reading frame containing residues encoding the N-terminal sequence with a termination codon at the nucleotide 894 followed by a polyadenylation signal (AATAAA). There are three ATG codons in this reading frame in the first 200 nucleotides of the cDNA with no upstream stop codons. However, only the second, at position 64, meets the criteria of Kozak (1989) for initiation of translation. Thus, using codon 64 as the start codon, the open reading frame would encode a protein of 310 amino acides with a predicted molecular wieght of ≈34 kDa. A fragment of the murine cDNA was used as a probe to isolate a full-length human cDNA clone for EMAPII from a lambda gt11 U937 monocyte library (FIGS. 4A–4D). Compared with murine EMAPII, the human cDNA was 86% identical, and the deduced sequence contained an additional two amino acids. The ATG designated as the start codon and the upstream ATG are both conserved in the human cDNA.

Since the N-terminal sequence obtained from the purified EMAPII is encoded by an internal sequence of the EMAPII clone, it was predicted that mature EMAPII results from processing from a larger polypeptide. The cDNA corresponding to the N-terminal, processed portion of the sequence encodes 165 amino acids which would result in a polypeptide of ≈18 kDa, in close agreement with the ≈22 kDa observed for EMAPII purified from meth A sarcoma cells. Although EMAPII is apparently secreted by meth A sarcoma cells, a hydropathy analysis of the predicted murine primary amino acid sequence lacked evidence for a hydrophobic signal peptide. Of note is that, both the predicted size of the protein before cleavage, as well as the cleavage site of this protein, are reminiscent of another secreted cytokine which also lacks a classical signal peptide, interleukin-1β (IL-1β). The mRNA for IL-1β encodes a 31 kDA precursor to the mature 17 kDA from (March et al, 1985), and proteolytic processing releases a 17 kDa secreted, active IL-1β (Black, 1989). An Asp in the P1 position of IL-1β is necessary for cleavage by the cysteine protease IL-1B converting enzyme (ICE) to yield the active 17 kDa IL-1β (Thronberry et al, 1992; Cerretti, 1992). In EMAPII, an Asp is present in the P1 position in both the murine and the human forms (FIGS. 4A–4D, arrow). Thus, a cystine protease similar or identical to ICE might be responsible for producing mature EMAPII from its pro-from. Supportive of the idea that the mature form is the biologically active protein, sequence conservation is 95% between the murine and the human region of the mature polypeptide, but drops to 74% in the putatuive pro-region.

The primary amino acid sequence of EMAPII shows little homology to any other proteins in the data banks. Nevertheless, a limited resemblance exists between residues in the N-terminal portion of EMAPII and several other cytokines, notably IL-8 and IL-1β, as well as von Willebrand antigen II, a product released by activated platelets and endothelial cells. All of these molecules share chemoattractant properties towards neutrophils and/or monocytes (Yoshimira, 1987; Sauder, (18)). For IL-8, Hebert et al (1991) have demostrated by in vitro mutagenesis that changing residues in this area, E31, L32, R33, or I37, to alanine resulted in a molecule incapable of mobilizing calcium in neutrophils and having reduced ability to compete with native IL-8 for binding to neutrophil IL-8 receptors.

Expression of Murine EMAPII in *E coli*. *E. coli* transfected with the portion of the EMAPII cDNA corresponding to mature EMAPII were pelleted by centrifugation, sonicated in the presence of tris-buffered saline, and the supernatants chromatographed on FPLC Mono Q. The peak containing EMAPII activity was identified based on the induction of tissue factor activity in ECs. In contrast, little protein eluted at a similar salt concentration from material obtained from *E. coli* transformed with vector alone, and this small peak had no significant tissue factor inducting activity. The material from the Mono Q activity peak of the *E. coli* transfected with the construct containing EMAPII cDNA was pooled, concentrated, and subjected to nonreduced SDS-PAGE. Silver staining revealed a complex pattern of bands, although elution of material from an identical lane of the gel demonstrated that only material with Mr ≈18 kDa had the capacity to induce tissue factor in ECs. This material was re-run on SDS-PAGE, and a single band was observed under both reduced and non-reduced conditions, the latter having the capacity to induce EC tissue factor. Western analysis with an antibody raised to a peptide comprising ASRLDLRIGRIVTAK of EMAPII visualized the ≈18 kDa band purified from *E. coli* transfected with the EMAPII cDNA, whereas no band was observed when the control vector was used.

D. TREATMENT OF TUMORS

Experiment 1: Localized Thrombohemorrhage

Normal C3H/He mice were injected intradermally with 20 micrograms of EMAP II. Each mouse received 100 micrograms of endotoxin, systemically, either 9, 15, or 18 hours after the EMAP II. Skin was harvested three hours later. In each case, localized hemorrhage was observed in the skin, at the site of the initial EMAP II injection.

Experiment 2: Localized Thrombohemorrhage

Normal Balb/C mice were injected intradermally with 20 micrograms EMAP II. Each mouse received 100 micrograms of endotoxin, systemically, either 18 or 24 hours after the EMAP II. Skin was harvested three hours later. In each case, localized hemorrhage was observed in the skin, at the site of the initial EMAP II injection.

Experiment 3: Hemorrhage in Meth A Fibrosarcomas

Methycholanthrene A-induced fibrosarcomas (meth A) were raised in the backs of C3H/He mice by intradermal injection of $2 \times 10^5$ tumor cells. Seven days later, mice were given a single intratumor injection of either purified recombinant human Tumor Necrosis Factor (TNF, 5 micrograms, in a PBS/albumin vehicle), heat treated TNF (inactivated by 15 minutes in a boiling water bath), EMAP II (20 micrograms in the vehicle), heat-treated EMAP II, or vehicle solution alone. Six hours after injection, mice were sacrificed and tumors were observed for the presence of gross hemorrhage. EMAP II elicited gross hemorrhage in a proportion of tumors comparable to TNF, but the controls were without appreciable effect. (FIG. 5).

Experiment 4: Hemorrhage in Mouse Mammary Carcinomas (Single Injections)

Figure 6:
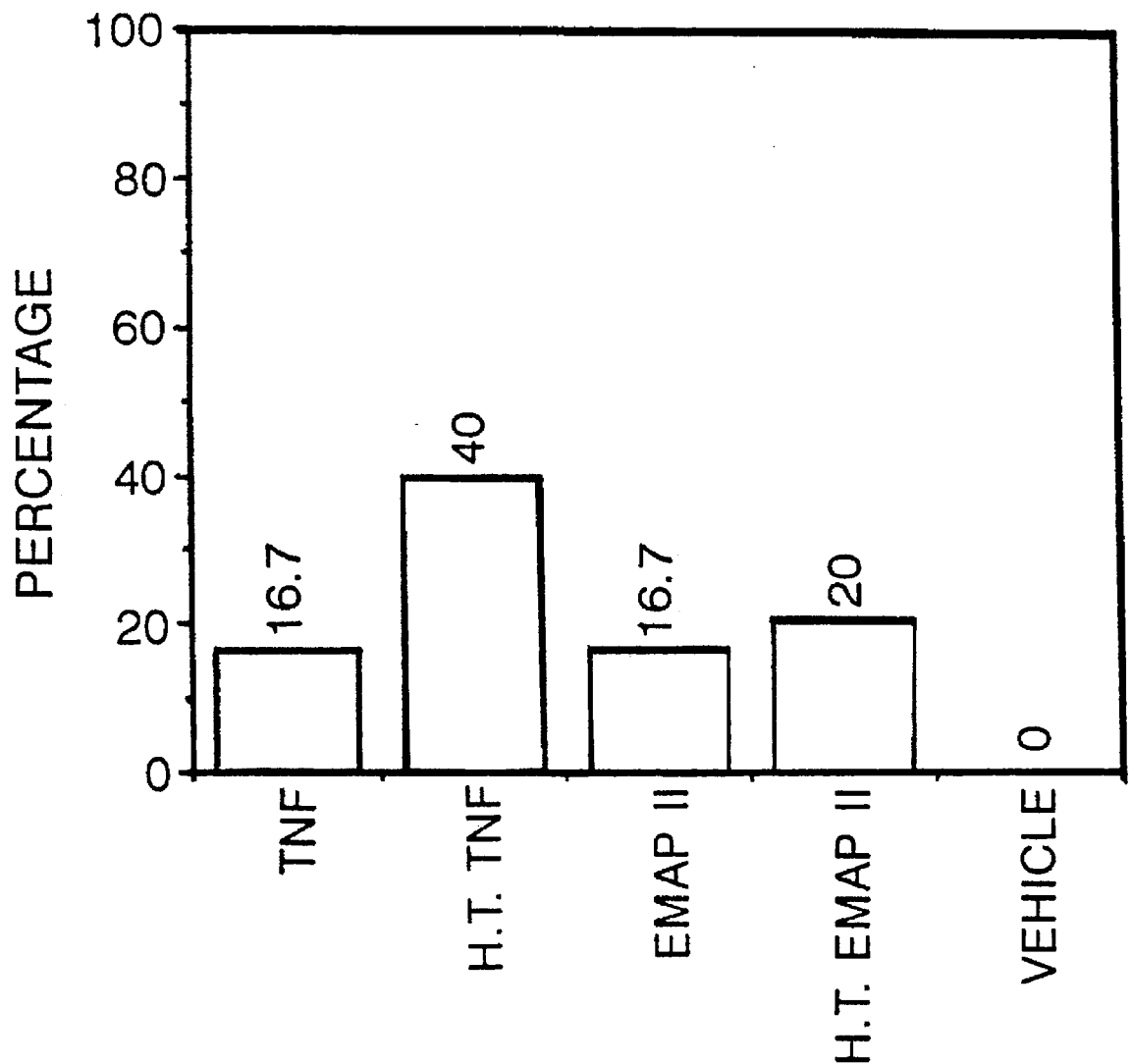
FIG. 6: Percentage of Mouse Mammary Carcinoma Demonstrating Gross Hemorrhage Six Hours After Single Injection

Mouse mammary carcinomas derived from MC2 cell line were raised in the backs of C3H/He mice by intradermal injection of $10^6$ tumor cells. Seven days later, mice were given a single intratumor injection of 5 micrograms TNF, heat-treated TNF, 20 micrograms EMAP II, heat-treated EMAP II, or vehicle alone. Six hours later, mice were sacrificed and tumors were observed for the presence of gross hemorrhage. No treatment elicited hemmorhage above baseline. (FIG. 6).

Experiment 5: Hemorrhage in Mouse Mammary Carcinomas (Dual Injections)

Figure 7:
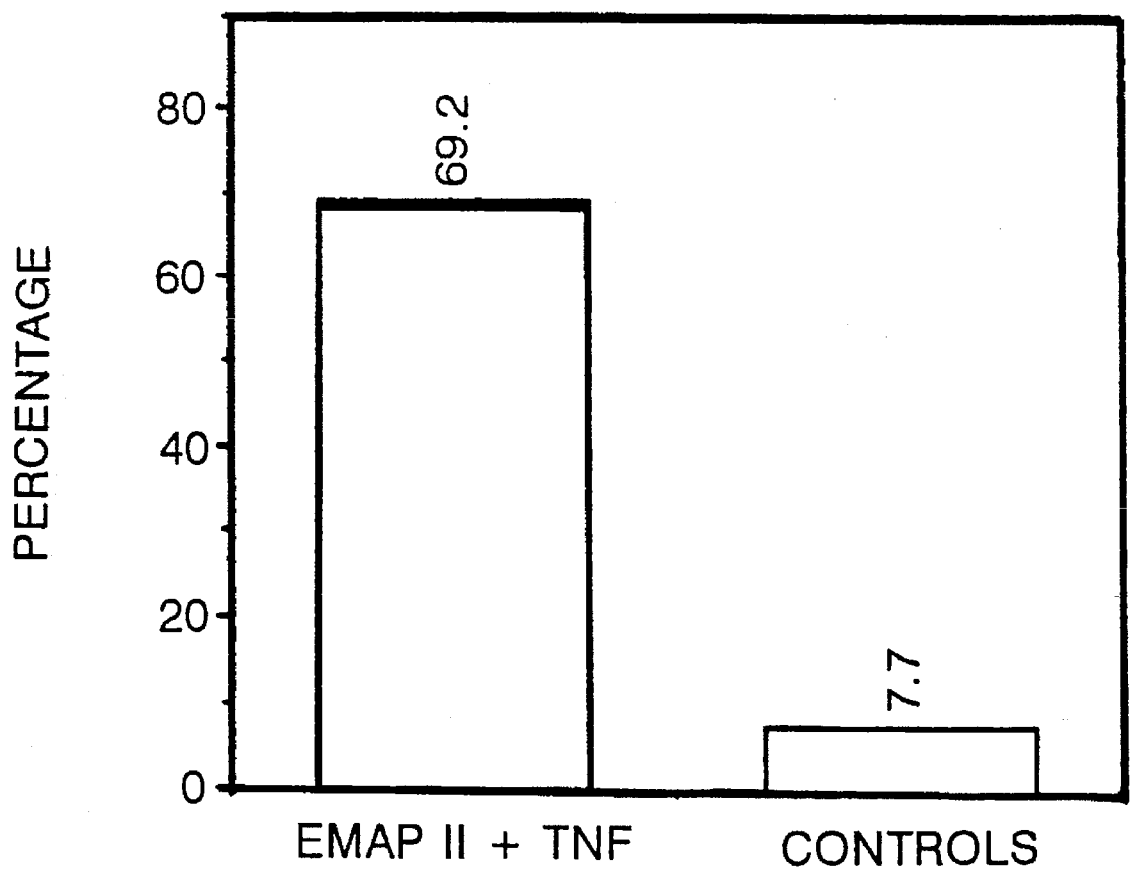
FIG. 7: Percentage of Mouse Mammary Carcinoma Demonstrating Gross Hemorrhage Six Hours After EMAP II+TNF Treatment
Figure 8B:
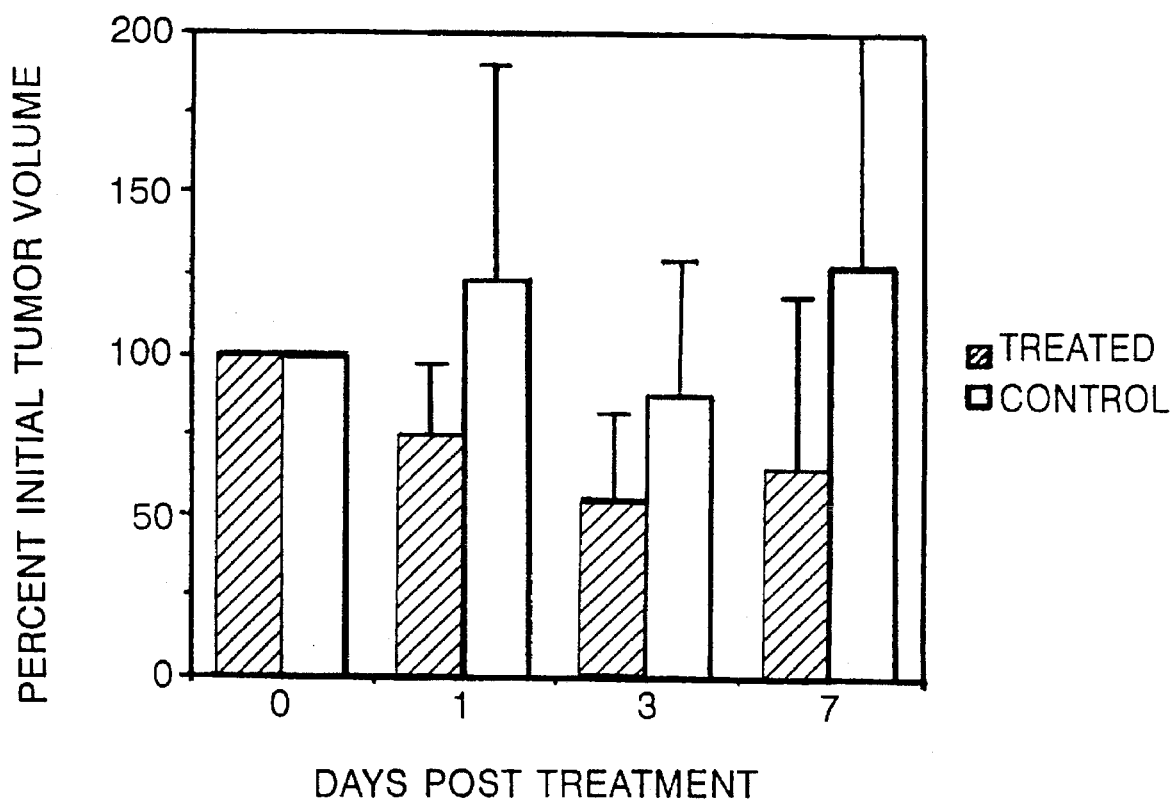
Figure 8C:
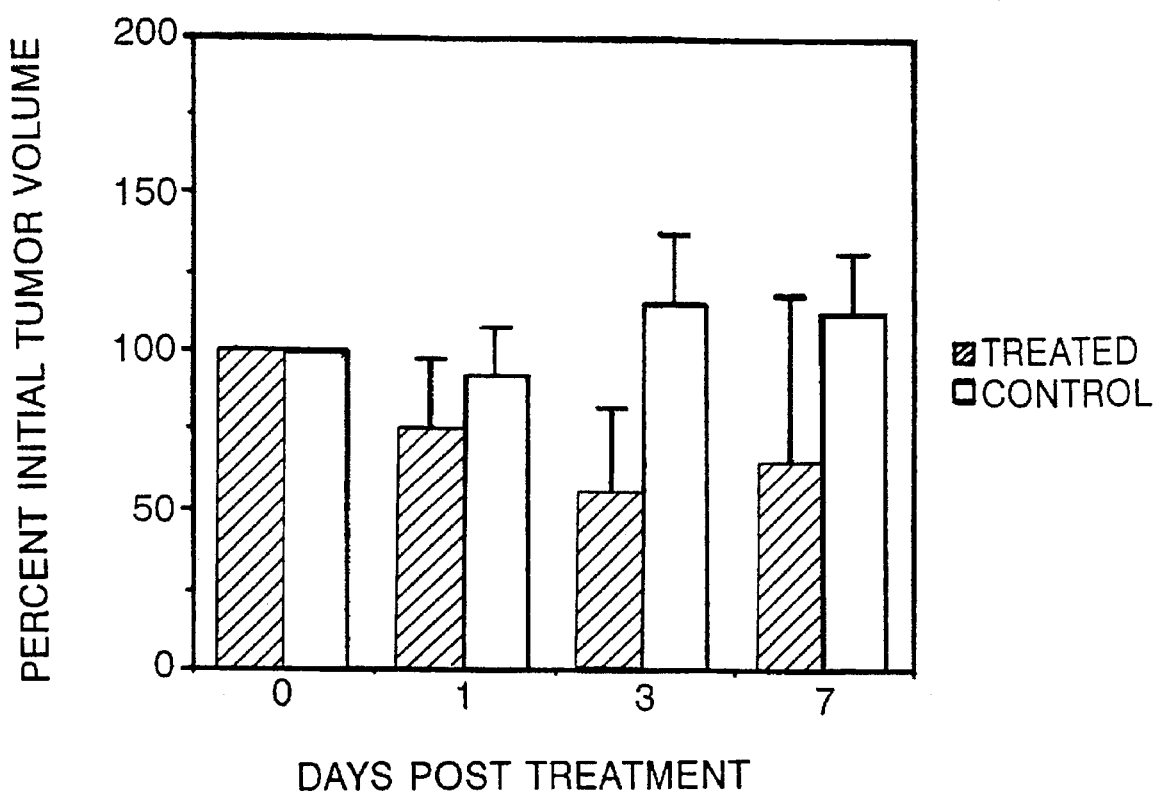
Figure 8D:
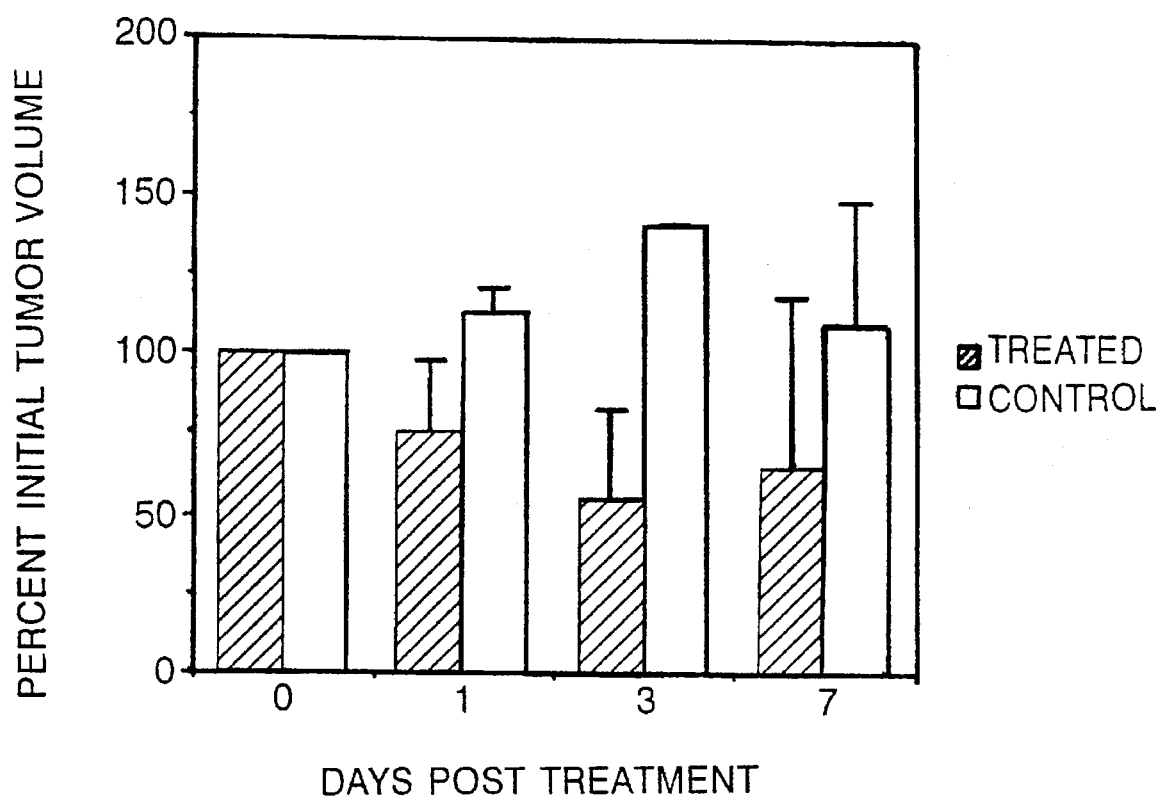
Figure 8E:
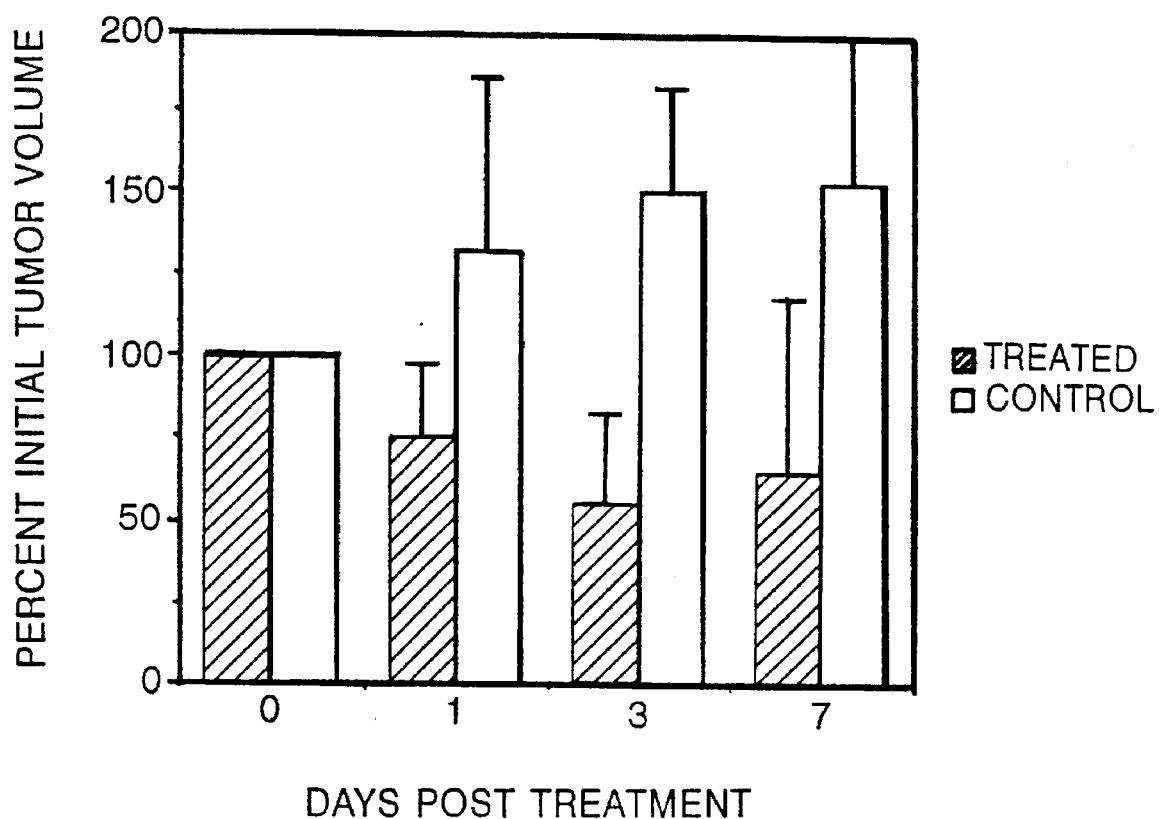

Mouse mammary carcinomas derived from the MC2 cell line were raised in the backs of C3H/He mice by intradermal injection of $10^6$ tumor cells. Six days later, mice received intratumor injections of 20 micrograms EMAP II followed 12–18 hours later by a systemic dose of 5 micrograms TNF. Control animals received combinations of either heat-treated (H.T.) EMAP II+TNF, EMAP II+H.T. TNF.H.T. EMAP II+H.T. TNF, or vehicle+TNF. Tumors wre excised six hours following the second (systemic) injection and examined for the presence of gross hemorrhage. (FIG. 7).

Experiment 6: Tumor Regression Following EMAP II+TNF Treatment

Mouse mammary carcinomas were treated as in experiment 5 with a local injection of 20 micrograms EMAP II followed 12–18 hours later by a systemic dose of 5 micrograms TNF, with control animals receiving heat-treated cytokines or vehicle. Length, width and height of each tumor was measured prior to the systemic dose and again on days 1, 3, and 7 after the systemic injection. Tumor volume was calculated by assuming the shape of each tumor was that of a spherical segment, and according to the formula:

$$V = (pi/6)h(h^2 + 3a^2),$$

where a is taken as half the average of the length and width of the tumor base. EMAP II+TNF treatment is compared with each combination of heat-inactivated control, as well as to vehicle+TNF. (FIGS. 8A–E).

Figure 9:
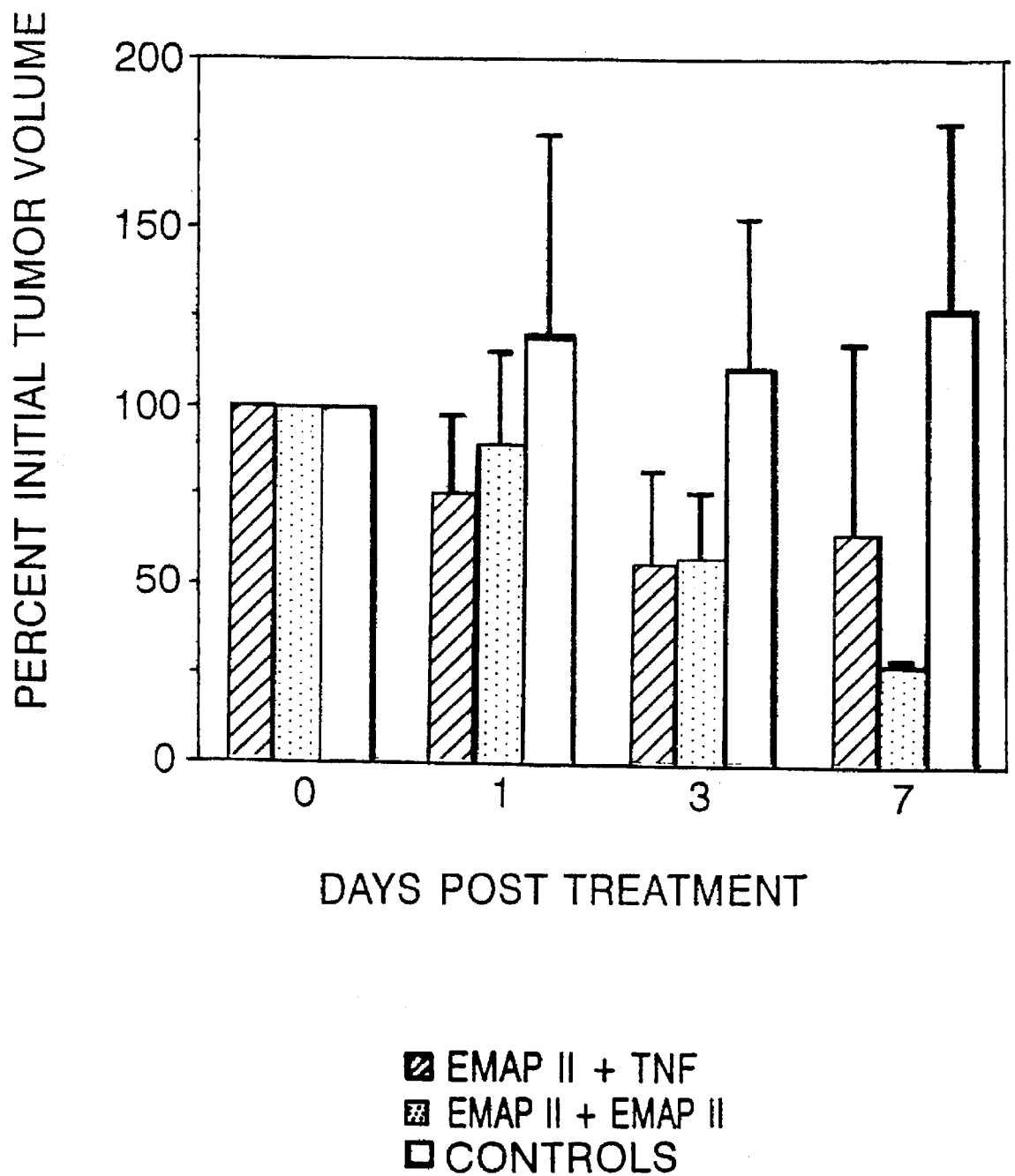
FIG. 9: Tumor Regression After EMAP II+EMAP II Treatment vs. Tumor Regression After EMAP II+TNF Treatment

Experiment 7: Tumor Regression Following EMAP II+EMAP II Treatment vs. Tumor Regression Following EMAP II+TNF Treatment Mouse mammary carcinomas were raised as above but given a local injection of 20 micrograms EMAP II followed 12–18 hours later by a systemic dose of 40 micrograms EMAP II. Tumor volume was calculated as in Experiment 6, and comparison was made with control tumors as well as EMAP II+TNF-treated tumors from Experiment 6. Local EMAP II followed by systemic EMAP II produced tumor regression to a greater degree than local EMAP II followed by systemic TNF. (FIG. 9).

Experiment 8: Clonogenic Cell Viability Assay (2, 3) Following EMAP II+TNF

Figure 10:
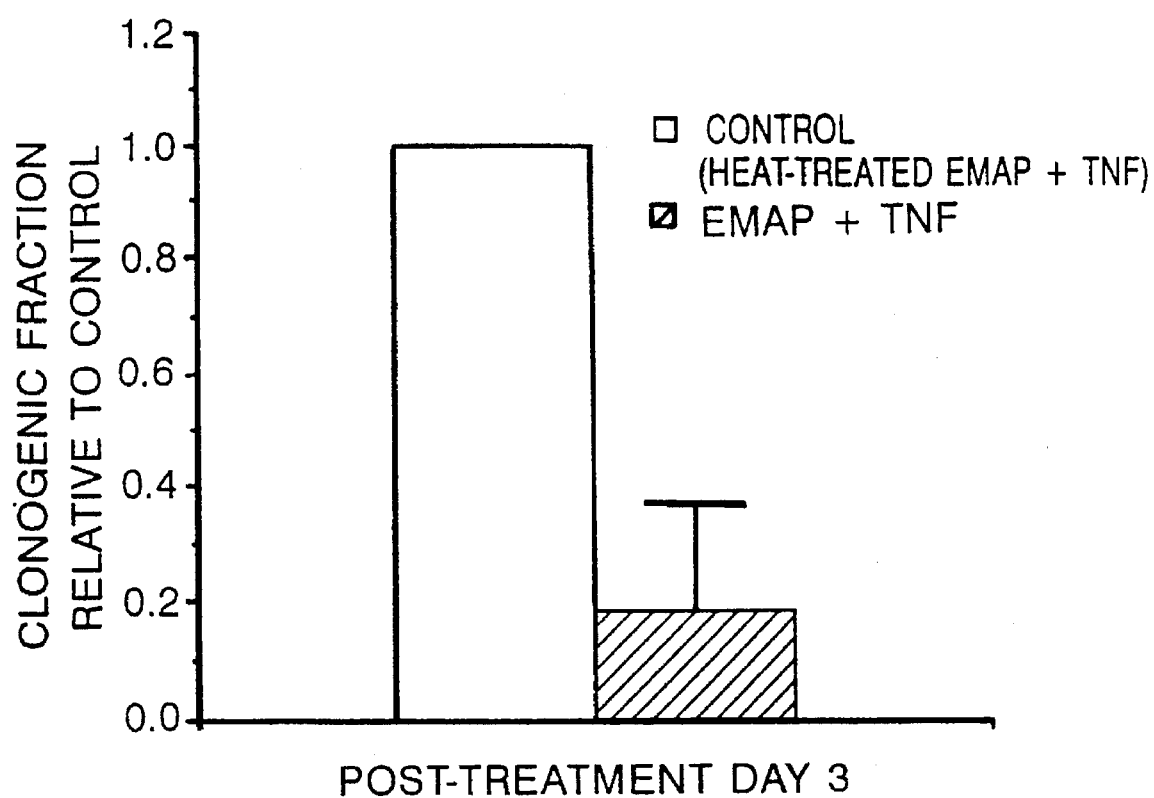
FIG. 10: Clonogenic Assay

Mouse mammary carcinomas were raised as above and treated with 20 micrograms EMAP II by intratumor injection, followed 18 hours later by 5 micrograms TNF by systemic injection. On the third day after treatment, tumors were aseptically excised, digested, and washed; cells were counted and placed in culture medium for four days, at which time the number of dividing colonies was assessed. The number of dividing colonies divided by the number of cells retrieved from the tumors was taken as the surviving clonogenic fraction; this was compared with the surviving clonogenic fraction from tumors treated with heat-inactivated EMAP II plus active TNF. (FIG. 10).

REFERENCES

A. Endothelial Monocyte Activating Polypeptide II

1. Quintana, A., E. Raczyka, Z. Latellio, and M. Donati. 1983. Eur. J. Cancer Clin. Oncol. 19:1031–1035.
2. Murray, J., K. Smith and G. Thurston. 1989. Brit. J. of Cancer 60:729–733.
3. Old., L. 1986. Science 230:630–632.
4. Haranaka, K., N. Satomi, and A. Sakurai. 1984. Int. J. Cancer 34:263–267.
5. Asher, A., J. Mule, C. Reichert, E. Shiloni, and S. Rosenberg. 1987. J. Immunol. 138:963–974.
6. Palladino, Jr., M., M. Shalaby, S. Kramer, D. Ferraiolo, R. Baughman, A. Deleo, D. Crase, B. Marifino, B. Aggarwal, I. Figari, D. Liggitt, and J. Patton. 1987. J. Immunol. 138:4023–4032.
7. Nawroth, P., D. Handley, G. Matsueda, R. De Waal, H. Gerlach, D. Blohm, and D. Stern. 1988. J. Exp. Med. 168:6637–647.
8. Sugarman, B. J., B. B. Aggarwal, P. Hass, I. Figari, M. Palladino, and H. Shepard. 1985. Science 230:943–945.
9. Clauss, M., J. Murray, M. Vianna, R. De Waal, G. Thurston, P. Nawroth, H. Gerlach, M. Gerlach, R. Bach, P. Familletti, and D. Stern. 1990. J. Biol. Chem. 265:7078–7083.
10. Clauss, M., J. Kao, S. Koga, J. Brett, J. Ryan, and D. Stern. 1991. Blood 78:376(Abstract).
11. Old, L., B. Benacerraf, D. Clarke, E. Carswell, and E. Stockert. 1961. Cancer Res. 21:1281–1300.
12. Familletti, P., and J. Fredericks. 1988. BioTechnology 6:41–44.
13. Jaffe, E., R. Nachman, C. Becker, and C. Minick. 1973. J. Clin. Invest. 52:2745–2753.
14. Thornton, S., S. Mueller, and E. Levine. 1983. Science 222:623–626.
15. Laemmli, U. 1970. Nature 227:680–685.
16. Matsudaira, P. 1987. J. Biol. Chem. 262:10035–10038.
17. Devereux, J., P. Haeberli, O. Smithies. 1984. Nucleic Acids Res. 12:387–395.
18. Anderson, P. 1985. Anal. Biochem. 148:105–110.
19. Humphreys, M., and S. Hopkins. 1989. J. Immunol. Methods 120:271–276.
20. Ruff, M., and G. Gifford. 1980. J. Immunol. 125:1671–1677.
21. Lerner, R., N. Green, H. Alexander, F. T. Liu, J. G. Sutchiffe, and T. Shinnick, 1981. Proc. Natl. Acad. Sci. (USA) 78:3403–3407.
22. Clauss, M., M. Gerlach, H. Gerlach, J. Brett, F. Wang, P. Familletti, Y-C. Pan, J. Olander, D. Connolly, and D. Stern. 1990. J. Exp. Med. 172:1535–1545.
23. Towbin, H., T. Staehelin, and J. Gordon. 1979. Proc. Natl. Acad. Sci. (USA) 76:4350–4364.
24. Johnson, D. A., J. W. Gautsch, J. R. Sportsman, and J. H. Elder. 1984. Gene Anal. Tech 1:3–8.
25. Kaye, J., S. Porcelli, J. Tite, J. Barry, and C. Janeway. 1983. J. Exp. Med. 158:836–856.
26. Bach, R., R. Gentry, and Y. Nemerson. 1986. Biochemistry 25:4007–4020.
27. Chomczynski, P., and N. Sacchi. 1987. Anal. Biochem. 162:156–159.
26. Conway, E., R. Bach, R. Rosenberg, and W. Konigsberg. 1989. Thromb. Res. 53:231–241.
29. Maier, J., P. Voulalas, D. Roeder, and T. Maciag. 1990. Science 249:1570–1574.
30. Quinn, M., S. Parthasarathy, L. Fong, and D. Steinberg. 1987. Proc. Natl. Acad. Sci. (USA) 84:2995–2998.
31. Granstein, R., R. Margolis, S. Mizel, and D. Sauder. 1986. J. Clin. Invest. 77:1020–1027.

32. McCarroll, D., E. Levin, and R. Montgomery. 1985. J. Clin. Invest. 75:1089–1095.
33. Verweij, C., P. Diergaarde, M. Hart, and H. Pannekoek. 1986. EMBO J. 5:1839–1847.
34. Bevilacqua, M., J. Pober, G. Majeau, R. Cotran, and M. Gimbrone. 1984. J. Exp. Med. 160:618–623.
35. Nawroth, P., D. Handley, C. Esmon, and D. Stern. 1986. Proc. Natl. Acad. Sci. 83:3460–3464.
36. Nawroth, P. and D. Stern. 1986. J. Exp. Med. 164:740–745.
37. Bevilacqua, M., J. Pober, G. Majeau, W. Fiers, R. Cotran, and M. Gimbrone. 1986. Proc. Natl. Acad. Sci. (USA) 83:4533–4537.
38. Dvorak, H. 1986. New Engl. J. Med. 315:1650–1658.
39. Dvorak, H., A. Dvorak, E. Manseau, J. Wiberg, and W. Churchill. 1979. J. Natl. Cancer Inst. 62:1459–1466.
40. Karpati, R., S. Banks, B. Malissen, S. Rosenberg, M. Sheard, J. Weber, and R. Hodes. 1991. J. Immunol. 146:2043–2051.
41. Webb, D., H. Mostowski, and T. Gerrard. 1991. J. Immunol. 146:3682–3686.
42. Senger, D., S. Galli, A. Dvorak, C. Perruzii, V. Harvey, and H. Dvorak. 1983. Science 219:983–985.
43. Keck, P., S. Hauser, G. Krivi, K. Sanzo, T. Warren, J. Feder, and D. Connolly. 1989. Science 246:1309–1312.
44. Connolly, D., D. Heuvelman, R. Nelson, J. Olander, B. Eppley, J. Delfino, N. Siegel, R. Leimbruber, and J. Feder. 1989. J. Clin. Invest. 84:1470–1478.
45. Ferrara, N., and W. Henzel. 1989. Biochem. Biophys. Res. Comm. 161:851–858.
46. Leung, D., G. Cachianes, W-J. Kuang, D. Goeddel, N. Ferrara. 1989. Science 246:1306–1309.

B. Peptide Derived from Amino Terminus of EMAP II

1. Dvorak, H. (1986) New Engl. J. Med. 315, 1650–1658.
2. Dvorak, H., Dvorak, A., Manseau, E., Wiberg, J., and Churchill, W. (1979) J. Natl. Cancer Inst. 62, 1459–1466.
3. Karpati, R., Banks, S., Malissen, B., Rosenberg, R., Sheard, M., Weber, J., and Hodes, R. (1991) J. Immunol. 146,2043–2051.
4. Old, L. (1990). In *Tumor Necrosis Factor: Structure, Mechanism of Action, Role in Disease, and Therapy*. Eds. Bonavida, B. and Granger. Publ. S. Karger, Basel. pp 1–30.
5. Clauss M., Murray, J., Vianna, M., DeWaal, R., Thurston, G., Nawroth, P., Gerlach, H., Gerlach, M., Bach, R., Familletti, P., and Stern, D. (1990) J. Biol. Chem. 265:7078–7083.
6. Clauss, M., Gerlach, M., Gerlach, H., Brett, J., Wang, F., Familletti, P., Yan, Y-C., Olander, J., Connolly, D., and Connolly, D. (1990) J. Exp. Med. 172:1535–1545.
7. Kao, J., Ryan, J., Brett, J., Chen, J., Shen, H., Fan, Y-G., Godman, G., Familletti, P., Wang, F., Pan, Y-C., Stern, D. and Clauss, M. (1992) J. Biol. Chem. 267:20239–20247.
8. Keck, P., Hauser, S., Krivi, G., Sanzo, K., Warren, T., Feder, J., and Connolly, D. (1989) Science 246, 1309–1312.
9. Senger, D., Galli, S., Dvorak, A., Perruzzi, C., Harvey, V., and Dvorak, H. (1983) Science 219,983–985.
10. Connolly, D., Heuvelman, D., Nelson, R., Olander, J., Epley, B., Delfino, J., Siegel, N., Leimbruber, R., and Feder, J. (1989) J. Clin. Invest. 84:1470–1478.
11. Brock, T., Dvorak, H., and Senger, D. (1991) Am. J. Pathol. 138, 213–221.
12. Leung, D., Cachianes, G., Kuang, W-J., Goeddel, D., and Ferrara, N. (1989) Science 246, 1306–1309.
13. Shen, H., Clauss, M., Ryan, J., Schmidt, A-M., Tijburg, P., Bordon, L., Connolly, D., Stern, D. and Kao, J. (1993) Blood 81, 2767–2773.
14. Fay, P., Kawai, Y., Wagner, D., Ginsburg, D., Bonthron, D., Ohlsson-Wilhelm, B., Chavin, S., Abraham, G., Handing, R., Orkin, S., Montgomery, R., and Marder, J. (1986) Science 232, 995–998.
15. Bonthron, D., Handin, R., Kaufman, R., Wasley, L., Orr, E., Mitsick, L., Ewenstein, B., Loscalzo, J., Ginsburg, D., and Orkin S. (1986) Nature 324,270–273.
16. Scott, J., and Montgomery, R. (1982) Blood 58, 1075–1080.
17. Wagner, D., and Bonfanti, R. (1991) Mayo Clin. Proc. 66,621–627.
18. Tijburg, P., Kao, J., Yah, S-D., van Mourik, J., and Stern, D. (1992) Circ. 86 (suppl I), #1627.
19. Clark-Lewis, I., Schumacker, C., Baggiolini, M., and Moser, B. (1991) J. Biol. Chem. 266, 23128–23134.
20. Herbert, C., Vitangcol, R., and Baker, J., (1991) J. Biol. Chem. 266, 18989–18994.
21. Moser, B., Dewald, B., Barella, L., Schumacker, C., Baggioini, M., and Clark-Lewis, I. (1993) J. Biol. Chem. 268, 7125–7128.
22. Barany, G., and Merrified, R., (1980) in *The Peptides*. Gross, E., and Meienhofer, J. Eds. Academic Press, NY. pp. 281–284.
23. Fraker, P., and Speck, J., (1978) Biophys. Res. Commun. 80, 849–857.
24. Boyum, A. (1968) Scand. J. Lab. Invest. 21 (Suppl. 97), 77–81.
25. Fluks, A. (1981) J. Immunol. Methods 41, 225–233.
26. Jaffe, E., Nachman, R., Becker, C., and Minick, R. (1973) J. Clin. Invest. 52, 2745–2756.
27. Thornton, S., Mueller, S., and Levine, E. (1983) Science 222, 623–625.
28. Shreeniwas, R., Koga, S., Karakurum, M., Pinsky, D., Kaiser, E., Brett, J., Wolitzky, C., Norton, C., Plocinski, J., Benjamin, W., Burns, D., Goldstein, A., and Stern, D. (1992) J. Clin. Invest. 90, 2333–2339.
29. Quinn, M., Parthasarathy, S., Fong, L., and Steinberg, D. (1987) PNAS(USA) 84, 2995–2998.
30. Harvath, L., Falk, W., and Leonard, E. (1980) J. immunol. Meth. 37, 39–45.
31. Kondo, S., and Kisiel, W. (1987) Blood 70, 1947–1954.
32. Greenberg, S., DiVirgilio, F., Steinberg, T., and Silverstein, S. (1988) J. Biol. Chem. 263, 10337–10343.
33. DiVirgilio, F., Meyer, B., Greenberg, S., and Silverstein, S. (1988) J. Cell Biol. 106,657–666.
34. DiVirgilio, F., Steinberg, T., and Silverstein, S. (1990) Cell Calcium 11, 57–62.
35. Menegazzi, R., Zabucchi, G., Knowles, A., Cramer, R., and Patriarca, P. (1992) J. Leuk. Biol. 52, 619–624.
36. Klotz, I., and Hunston, D. (1984) J. Biol. Chem. 258, 11442–11445.
37. Montesano, L., Cawley, D., and Herschman, H. (1982) Biochem. Biophys. Res. Commun. 109, 7–13.
38. Laemmli, U. (1970) Nature 227, 680–685.
39. Kloczewiak, M., Timmons, S., and Hawiger, J. (1987) Biochemistry 26, 6152–6156.
40. Kay, J., Porcelli, S., Tite, J., Barry, J., and Janeway, C. (1983) J. Exp. Med. 158, 836–856.
41. Granstein, R., Margolis, R., Mizel, S., and Sauder, D. (1986) J. Clin. Invest. 77, 1020–1027.
42. Matsushima, K., Morishita, K., Yoshimura, T., Lavu, S., Obayashi, Y., Lew, W., Appella, E., Kung, H., Leonard, E., and Oppenheim. (1988) J. Exp. Med. 167, 1883–1893.
43. Baggiolini, M., and Clark-Lewis, I. (1992) FEBS Lett. 307, 97–101.
44. Schiffman, E., Corcoran, B., and Wahl, S. (1975) PNAS (USA) 72, 1059–1062.

45. Ming, W., Bersani, L., and Mantovani, A. (1987) J. Immunol. 138, 1469–1474.
46. Durum, S., Schmidt, J., and Oppenheim, J. (1985) Annu. Rev. Immunol. 3, 263–287.
47. Pennica, D., Nedwin, G., Hayflick, J., Seeburg, P., Derynck, R., Palladino, M., Kohr, W., Aggarwal, B., and Goeddel, D. (1984) Nature 312, 724–729.
48. Oppenheim, J., Zachariae, C., Mukaida, N., and Matsushima, K. (1991) Annu. Rev. Immunol. 9,617–648.

D. TREATMENT OF TUMORS

1. Vaage J. and Pepin K. G., Morphological Observations during Developing Concomitant Immunity against a C3H/He Mammary Tumor. Cancer Research 45, 659–66 February 1985.
2. Twentyman P. R. Brown J. M., Franko A. J., Scoles M. A., and Kallman R. F., A New Mouse Tumor Model System (RIF-1) for Comparison of End-Point Studies. JNCI, Vol 64(3), 595–604, March 1980.
3. Braunschweiger P. G., Kumar N., Constantinidis I., Wehrle J. P., Glickson J. D., Johnson C. S., and Furmanski P., Potentiation of Interleukin 1-alpha Mediated Antitumor Effects by Ketoconazole. Cancer Research 50, 4709–17, August 1990.

What is claimed is:

1. An antibody which specifically binds to endothelial monocyte activating polypeptide II, wherein the endothelial monocyte activating polypeptide II is characterized by:

an apparent molecular weight of about 20 kilodaltons by SDS-PAGE;

the ability to induce tissue factor by endothelial cells and monocytes; and comprises the amino acid sequence Gly-Lys-Pro-Ile-Asp -Ala-Ser-Arg-Leu-Asp-Leu- Arg-Ile-Gly-Xaa-Ile-Val-Thr-Ala-Lys (SEQ ID NO: 1).

2. The antibody of claim 1 wherein the antibody is a polyclonal antibody.

3. The antibody of claim 1 wherein the antibody is a monoclonal antibody.

4. A method of obtaining an antibody which specifically binds to endothelial monocyte activating polypeptide II, comprising:

a) immunizing a rabbit with a peptide comprising the amino acid sequence Gly-Lys-Pro-Ile-Asp-Ala-Ser-Arg-Leu-Asp-Leu-Arg-Ile-Gly-Cys -Ile-Val-Thr-Ala-Lys (SEQ ID NO: 2) coupled to keyhole limpet hemocyanin; and b) obtaining purified IgG from the rabbit.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
      ( A ) LENGTH: 20 amino acids
      ( B ) TYPE: amino acid
      ( C ) TOPOLOGY: linear ( i i ) MOLECULE TYPE: Peptide ( i i i ) SEQUENCE DESCRIPTION: SEQ ID NO:1:

```
Gly  Lys  Pro  Ile  Asp  Ala  Ser  Arg  Leu  Asp  Leu  Arg  Ile  Gly  Xaa  Ile
 1               5                            10                           15
Val  Thr  Ala  Lys
              20
```

( 2 ) INFORMATION FOR SEQ ID NO:2:

( i ) SEQUENCE CHARACTERISTICS:
      ( A ) LENGTH: 20 amino acids
      ( B ) TYPE: amino acid
      ( C ) TOPOLOGY: linear ( i i ) MOLECULE TYPE: Peptide ( i i i ) SEQUENCE DESCRIPTION: SEQ ID NO:2:

```
Gly  Lys  Pro  Ile  Asp  Ala  Ser  Arg  Leu  Asp  Leu  Arg  Ile  Gly  Cys  Ile
 1               5                            10                           15
Val  Thr  Ala  Lys
              20
```

( 2 ) INFORMATION FOR SEQ ID NO:3:

( i ) SEQUENCE CHARACTERISTICS:
      ( A ) LENGTH: 7 amino acids
      ( B ) TYPE: amino acid
      ( C ) TOPOLOGY: linear ( i i ) MOLECULE TYPE: Peptide ( i i i ) SEQUENCE DESCRIPTION: SEQ ID NO:3:

```
Arg  Ile  Gly  Arg  Ile  Val  Thr
 1               5
```

( 2 ) INFORMATION FOR SEQ ID NO:4:

( i ) SEQUENCE CHARACTERISTICS:
      ( A ) LENGTH: 10 amino acids
      ( B ) TYPE: amino acid (C) TOPOLOGY: linear (ii) MOLECULE TYPE: Peptide (iii) SEQUENCE DESCRIPTION: SEQ ID NO:4:

```
Arg Ile Gly Arg Ile Val Thr Ala Lys Tyr
1               5                   10
```

(2) INFORMATION FOR SEQ ID NO:5:

(i) SEQUENCE CHARACTERISTICS:
        (A) LENGTH: 15 amino acids
        (B) TYPE: amino acid
        (C) TOPOLOGY: linear (ii) MOLECULE TYPE: Peptide (iii) SEQUENCE DESCRIPTION: SEQ ID NO:5:

```
Ala Ser Arg Leu Asp Leu Arg Ile Gly Cys Ile Val Thr Ala Lys
1               5                   10                  15
```

(2) INFORMATION FOR SEQ ID NO:6:

(i) SEQUENCE CHARACTERISTICS:
        (A) LENGTH: 16 amino acids
        (B) TYPE: amino acid
        (C) TOPOLOGY: linear (ii) MOLECULE TYPE: Peptide (iii) SEQUENCE DESCRIPTION: SEQ ID NO:6:

```
Ala Ser Arg Leu Asp Leu Arg Ile Gly Arg Ile Val Thr Ala Lys Tyr
1               5                   10                  15
```

(2) INFORMATION FOR SEQ ID NO:7:

(i) SEQUENCE CHARACTERISTICS:
        (A) LENGTH: 15 amino acids
        (B) TYPE: amino acid
        (C) TOPOLOGY: linear (ii) MOLECULE TYPE: Peptide (iii) SEQUENCE DESCRIPTION: SEQ ID NO:7:

```
Ala Ser Arg Leu Asp Leu Arg Ile Gly Arg Ile Val Thr Ala Lys
1               5                   10                  15
```

(2) INFORMATION FOR SEQ ID NO:8:

(i) SEQUENCE CHARACTERISTICS:
        (A) LENGTH: 11 amino acids
        (B) TYPE: amino acid
        (C) TOPOLOGY: linear (ii) MOLECULE TYPE: Peptide (iii) SEQUENCE DESCRIPTION: SEQ ID NO:8:

```
Leu Arg Ile Gly Arg Ile Val Thr Ala Lys Tyr
1               5                   10
```

(2) INFORMATION FOR SEQ ID NO:9:

(i) SEQUENCE CHARACTERISTICS:
        (A) LENGTH: 7 amino acids
        (B) TYPE: amino acid
        (C) TOPOLOGY: linear (ii) MOLECULE TYPE: Peptide (iii) SEQUENCE DESCRIPTION: SEQ ID NO:9:

```
    Arg  Ile  Gly  Arg  Ile  Ile  Thr
    1              5
```

(2) INFORMATION FOR SEQ ID NO:10:

(i) SEQUENCE CHARACTERISTICS:
        (A) LENGTH: 7 amino acids
        (B) TYPE: amino acid
        (C) TOPOLOGY: linear (ii) MOLECULE TYPE: Peptide (iii) SEQUENCE DESCRIPTION: SEQ ID NO:10:

```
    Ala  Ile  Gly  Arg  Ile  Val  Thr
    1              5
```

(2) INFORMATION FOR SEQ ID NO:11:

(i) SEQUENCE CHARACTERISTICS:
        (A) LENGTH: 166 amino acids
        (B) TYPE: amino acid
        (C) TOPOLOGY: linear (ii) MOLECULE TYPE: Peptide (iii) SEQUENCE DESCRIPTION: SEQ ID NO:11:

```
Ser  Lys  Pro  Ile  Asp  Ala  Ser  Arg  Leu  Asp  Leu  Arg  Ile  Gly  Cys  Ile
1              5                        10                       15

Val  Thr  Ala  Lys  Lys  His  Pro  Asp  Ala  Asp  Ser  Leu  Tyr  Val  Glu  Glu
               20                       25                       30

Val  Asp  Val  Gly  Glu  Ala  Ala  Pro  Arg  Thr  Val  Val  Ser  Gly  Leu  Val
          35                       40                       45

Asn  His  Val  Pro  Leu  Glu  Gln  Met  Gln  Asn  Arg  Met  Val  Val  Leu  Leu
     50                       55                       60

Cys  Asn  Leu  Lys  Pro  Ala  Lys  Met  Arg  Gly  Val  Leu  Ser  Gln  Ala  Met
65                       70                       75                       80

Val  Met  Cys  Ala  Ser  Ser  Pro  Asp  Lys  Val  Glu  Ile  Leu  Ala  Pro  Pro
               85                       90                       95

Asn  Gly  Ser  Val  Pro  Gly  Asp  Arg  Ile  Thr  Phe  Asp  Ala  Phe  Pro  Gly
               100                      105                      110

Glu  Pro  Asp  Lys  Glu  Leu  Asn  Pro  Lys  Lys  Lys  Ile  Trp  Glu  Gln  Ile
          115                      120                      125

Gln  Pro  Asp  Leu  His  Thr  Asn  Ala  Glu  Cys  Val  Ala  Thr  Tyr  Lys  Gly
          130                      135                      140

Ala  Pro  Phe  Glu  Val  Lys  Gly  Lys  Gly  Val  Cys  Arg  Ala  Gln  Thr  Met
145                      150                      155                      160

Ala  Asn  Ser  Gly  Ile  Lys
               165
```

(2) INFORMATION FOR SEQ ID NO:12:

(i) SEQUENCE CHARACTERISTICS:
        (A) LENGTH: 7 amino acids
        (B) TYPE: amino acid
        (C) TOPOLOGY: linear (ii) MOLECULE TYPE: Peptide (iii) SEQUENCE DESCRIPTION: SEQ ID NO:12:

```
    Ala  Ile  Leu  Arg  Gln  Val  Thr
    1              5
```

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:13:

```
Leu Ala Ile Leu Arg Gln Val Thr
1               5
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:14:

```
Arg Ile Gly Arg Ile Val Thr
1               5
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:15:

```
Asp Leu Arg Ile Gln Arg Thr Val Thr Ala Ser
1               5                   10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:16:

```
Cys Arg Ala Gln Thr Met Ala Asn Ser Gly Ile Lys
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:17:

```
Ala Val Leu Pro Arg Ser Ala Lys Glu Leu Arg Leu
1               5                   10
```

( 2 ) INFORMATION FOR SEQ ID NO:18:

( i ) SEQUENCE CHARACTERISTICS:
        ( A ) LENGTH: 16 amino acids
        ( B ) TYPE: amino acid (C) TOPOLOGY: linear (ii) MOLECULE TYPE: Peptide (iii) SEQUENCE DESCRIPTION: SEQ ID NO:18:

Ile Arg Lys Asp Met Asp Lys Val Glu Thr Phe Leu Arg Ile Val Gln
1               5                   10                  15

(2) INFORMATION FOR SEQ ID NO:19:

(i) SEQUENCE CHARACTERISTICS:
        (A) LENGTH: 6 amino acids
        (B) TYPE: amino acid
        (C) TOPOLOGY: linear (ii) MOLECULE TYPE: Peptide (iii) SEQUENCE DESCRIPTION: SEQ ID NO:19:

Ala Ser Arg Leu Asp Leu
1               5

(2) INFORMATION FOR SEQ ID NO:20:

(i) SEQUENCE CHARACTERISTICS:
        (A) LENGTH: 7 amino acids
        (B) TYPE: amino acid
        (C) TOPOLOGY: linear (ii) MOLECULE TYPE: Peptide (iii) SEQUENCE DESCRIPTION: SEQ ID NO:20:

Arg Ile Gly Arg Ala Val Thr
1               5

(2) INFORMATION FOR SEQ ID NO:21:

(i) SEQUENCE CHARACTERISTICS:
        (A) LENGTH: 10 amino acids
        (B) TYPE: amino acid
        (C) TOPOLOGY: linear (ii) MOLECULE TYPE: Peptide (iii) SEQUENCE DESCRIPTION: SEQ ID NO:21:

Arg Ile Gly Arg Ile Val Thr Ala Lys Tyr
1               5                   10

(2) INFORMATION FOR SEQ ID NO:22:

(i) SEQUENCE CHARACTERISTICS:
        (A) LENGTH: 16 amino acids
        (B) TYPE: amino acid
        (C) TOPOLOGY: linear (ii) MOLECULE TYPE: Peptide (iii) SEQUENCE DESCRIPTION: SEQ ID NO:22:

Ala Ser Arg Leu Asp Leu Arg Ile Gly Arg Ile Val Thr Ala Lys Tyr
1               5                   10                  15

(2) INFORMATION FOR SEQ ID NO:23:

(i) SEQUENCE CHARACTERISTICS:
        (A) LENGTH: 13 amino acids
        (B) TYPE: amino acid
        (C) TOPOLOGY: linear (ii) MOLECULE TYPE: Peptide (iii) SEQUENCE DESCRIPTION: SEQ ID NO:23:

```
    Ala  Ser  Arg  Leu  Asp  Leu  Arg  Ile  Gly  Arg  Ile  Val  Thr
    1              5                        10
```

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:24:

```
    Xaa  Ile  Gly  Xaa  Ile  Val  Thr
    1              5
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:25:

```
    Xaa  Ile  Gly  Xaa  Ile  Ile  Thr
    1              5
```

( 2 ) INFORMATION FOR SEQ ID NO:26:

( i ) SEQUENCE CHARACTERISTICS:
        ( A ) LENGTH: 14 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:26:

```
    Ala  Ala  Arg  Cys  Cys  Asn  Ala  Thr  His  Gly  Ala  Tyr  Gly  Cys
    1              5                        10
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:27:

```
    Tyr  Thr  Thr  Asn  Gly  Cys  Asn  Gly  Thr  Asn  Ala  Cys  Asp  Ala  Thr
    1              5                        10                       15
```

( 2 ) INFORMATION FOR SEQ ID NO:28:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) ANTI-SENSE: N ( i v ) SEQUENCE DESCRIPTION: SEQ ID NO:28:

```
AAGCCCATTG ATGCCTCCCG GCTGGACCTG CGGATTGGCT GCATTGTGAC AGCCAAG          57
```

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO:29:

ATTTTGCATC TGTTCTAG                                                                                               18

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( C ) TOPOLOGY: linear ( i i ) MOLECULE TYPE: Peptide ( i i i ) SEQUENCE DESCRIPTION: SEQ ID NO:30:

Lys Pro Ile Asp Ala Ser Arg Leu Glu Leu
1                    5                          10

( 2 ) INFORMATION FOR SEQ ID NO:31:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO:31:

TATGAAACCA ATCGATGCAT CTCGTCTGGA TCTT                                     34

( 2 ) INFORMATION FOR SEQ ID NO:32:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO:32:

CGAAGATCCA GACGAGATGC ATCGATTGGT TTCA                                     34

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) SEQUENCE DESCRIPTION: SEQ ID NO:33:

CCACCCATGG CAAATTCCAT GGCA                                                             24

( 2 ) INFORMATION FOR SEQ ID NO:34:

( i ) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: DNA (genomic)

(iii) SEQUENCE DESCRIPTION: SEQ ID NO:34:

TCTAGACGGC AGGTCAGGTC CACC                                                    24

(2) INFORMATION FOR SEQ ID NO:35:

(i) SEQUENCE CHARACTERISTICS:
(A) LENGTH: 1086 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:35:

```
GAGGCTGCTC AAGAGCTGCG GTTGGGTCAC CGCTTCATGT TTCTCTGCCG ATTCTGGGA       60
AAGATGGCAA CGAATGATGC TGTTCTGAAG AGGCTGGAGC AGAAGGGTGC AGAGGCGGAT     120
CAGATCATCG AATATCTCAA GCAGCAGGTT GCTCTTCTTA AGGAGAAAGC AATTTTGCAG     180
GCAACAATGA GAGAAGAAAA GAAACTTCGA GTTGAAAATG CTAAACTGAA AAAAGAAATA     240
GAAGAGCTAA AGCAAGAGCT GATTCTGGCA GAAATTCATA ACGGAGTGGA GCAAGTGCGT     300
GTTCGATTGA GTACTCCACT GCAGACGAAC TGTACTGCTT CTGAAAGTGT GGTGCAGTCT     360
CCATCAGTAG CAACCACCGC CTCTCCTGCT ACAAAGAGC AGATCAAAGC GGGAGAAGAA      420
AAGAAGGTGA AAGAGAAGAC TGAAAAGAAA GGAGAGAAAA AGGAGAAGCA GCAGTCGGCA     480
GCAGCAAGTA CTGACTCCAA GCCTATCGAC GCATCGCGTC TGGATCTTCG AATTGGTTGT     540
ATTGTTACTG CCAAGAAGCA CCCTGATGCA GATTCACTGT ATGTGGAGGA AGTAGATGTG     600
GGAGAAGCAG CCCCGCGCAC GGTCGTCAGC GGGCTGGTGA ATCATGTTCC TCTAGAACAG     660
ATGCAAAATC GTATGGTGGT TTTACTCTGT AATCTGAAGC CTGCAAAGAT GCGGGGAGTT     720
CTGTCTCAAG CCATGGTGAT GTGTGCCAGT TCACCAGAGA AAGTGGAGAT TCTGGCCCCT     780
CCCAACGGGT CCGTTCCTGG GGACAGAATT ACTTTTGATG CTTTTCCTGG AGAGCCTGAC     840
AAGGAGCTAA ACCCTAAGAA GAAGATCTGG GAGCAGATCC AGCCTGACCT GCACACCAAT     900
GCTGAGTGTG TGGCCACATA CAAAGGAGCT CCCTTTGAGG TGAAGGGGAA GGGAGTTTGC     960
AGAGCCCAAA CCATGGCCAA TAGTGGAATT AAATAAGTGC TCTGTAACTG AAAGACATTG    1020
GCGAAAACTT AATAACAATA AAGAGAAGTG TGTTTATCAC TTACATATAA AAAAAAAAA    1080
AAAAAA                                                               1086
```

(2) INFORMATION FOR SEQ ID NO:36:

(i) SEQUENCE CHARACTERISTICS:
(A) LENGTH: 310 amino acids
(B) TYPE: amino acid
(C) TOPOLOGY: linear (ii) MOLECULE TYPE: protein (xi) SEQUENCE DESCRIPTION: SEQ ID NO:36:

```
Met Ala Thr Asn Asp Ala Val Leu Lys Arg Leu Glu Gln Lys Gly Ala
1               5                   10                  15
Glu Ala Asp Gln Ile Ile Glu Tyr Leu Lys Gln Gln Val Ala Leu Leu
            20                  25                  30
```

```
    Lys  Glu  Lys  Ala  Ile  Leu  Gln  Ala  Thr  Met  Arg  Glu  Lys  Lys  Leu
              35                      40                     45

Arg  Val  Glu  Asn  Ala  Lys  Leu  Lys  Lys  Glu  Ile  Glu  Glu  Leu  Lys  Gln
              50                      55                     60

Glu  Leu  Ile  Leu  Ala  Glu  Ile  His  Asn  Gly  Val  Glu  Gln  Val  Arg  Val
    65                            70                     75                     80

Arg  Leu  Ser  Thr  Pro  Leu  Gln  Thr  Asn  Cys  Thr  Ala  Ser  Glu  Ser  Val
                        85                      90                     95

Val  Gln  Ser  Pro  Ser  Val  Ala  Thr  Thr  Ala  Ser  Pro  Ala  Thr  Lys  Glu
                       100                     105                    110

Gln  Ile  Lys  Ala  Gly  Glu  Glu  Lys  Lys  Val  Lys  Glu  Lys  Thr  Glu  Lys
                   115                     120                    125

Lys  Gly  Glu  Lys  Lys  Glu  Lys  Gln  Gln  Ser  Ala  Ala  Ala  Ser  Thr  Asp
              130                     135                    140

Ser  Lys  Pro  Ile  Asp  Ala  Ser  Arg  Leu  Asp  Leu  Arg  Ile  Gly  Cys  Ile
    145                           150                    155                    160

Val  Thr  Ala  Lys  Lys  His  Pro  Asp  Ala  Asp  Ser  Leu  Tyr  Val  Glu  Glu
                        165                     170                    175

Val  Asp  Val  Gly  Glu  Ala  Ala  Pro  Arg  Thr  Val  Val  Ser  Gly  Leu  Val
                   180                     185                    190

Asn  His  Val  Pro  Leu  Glu  Gln  Met  Gln  Asn  Arg  Met  Val  Val  Leu  Leu
              195                     200                    205

Cys  Asn  Leu  Lys  Pro  Ala  Lys  Met  Arg  Gly  Val  Leu  Ser  Gln  Ala  Met
         210                     215                    220

Val  Met  Cys  Ala  Ser  Ser  Pro  Glu  Lys  Val  Glu  Ile  Leu  Ala  Pro  Pro
    225                           230                    235                    240

Asn  Gly  Ser  Val  Pro  Gly  Asp  Arg  Ile  Thr  Phe  Asp  Ala  Phe  Pro  Gly
                        245                     250                    255

Glu  Pro  Asp  Lys  Glu  Leu  Asn  Pro  Lys  Lys  Lys  Ile  Trp  Glu  Gln  Ile
                   260                     265                    270

Gln  Pro  Asp  Leu  His  Thr  Asn  Ala  Glu  Cys  Val  Ala  Thr  Tyr  Lys  Gly
              275                     280                    285

Ala  Pro  Phe  Glu  Val  Lys  Gly  Lys  Gly  Val  Cys  Arg  Ala  Gln  Thr  Met
         290                     295                    300

Ala  Asn  Ser  Gly  Ile  Lys
    305                     310
```

( 2 ) INFORMATION FOR SEQ ID NO:37:

( i ) SEQUENCE CHARACTERISTICS:
        ( A ) LENGTH: 310 amino acids
        ( B ) TYPE: amino acid
        ( C ) TOPOLOGY: linear ( i i ) MOLECULE TYPE: protein ( x i ) SEQUENCE DESCRIPTION: SEQ ID NO:37:

```
    Met  Ala  Asn  Asn  Asp  Ala  Val  Leu  Lys  Arg  Leu  Glu  Gln  Lys  Gly  Ala
    1                   5                       10                     15

Glu  Ala  Asp  Gln  Ile  Ile  Glu  Tyr  Leu  Lys  Gln  Gln  Val  Ser  Leu  Leu
                        20                      25                     30

Lys  Glu  Lys  Ala  Ile  Leu  Gln  Ala  Thr  Leu  Arg  Glu  Glu  Lys  Lys  Leu
              35                      40                     45

Arg  Val  Glu  Asn  Ala  Lys  Leu  Lys  Lys  Glu  Ile  Glu  Glu  Leu  Lys  Gln
              50                      55                     60

Glu  Leu  Ile  Gln  Ala  Glu  Ile  Gln  Asn  Gly  Val  Lys  Gln  Ile  Pro  Phe
    65                            70                     75                     80
```

```
Pro Ser Gly Thr Pro Leu His Ala Asn Ser Met Val Ser Glu Asn Val
                 85                   90                   95
Ile Gln Ser Thr Ala Val Ala Thr Thr Val Ser Ser Gly Thr Lys Glu
            100                 105                 110
Gln Ile Lys Ala Gly Asp Glu Lys Lys Ala Lys Glu Lys Ile Glu Lys
        115                 120             125
Lys Gly Glu Lys Lys Lys Gln Gln Ser Ile Ala Gly Ser Ala Asp
    130                 135                 140
Ser Lys Pro Ile Asp Ala Ser Arg Leu Asp Leu Arg Ile Gly Cys Ile
145             150                     155                 160
Ile Thr Ala Arg Lys His Pro Asp Ala Asp Ser Leu Tyr Val Glu Glu
                165                 170                     175
Val Asp Val Gly Glu Ile Ala Pro Arg Thr Val Val Ser Gly Leu Val
            180                 185                 190
Asn His Val Pro Leu Glu Gln Met Gln Asn Arg Met Val Ile Leu Leu
        195                 200                 205
Cys Asn Leu Lys Pro Ala Lys Met Arg Gly Val Leu Ser Gln Ala Met
    210                 215                 220
Val Met Cys Ala Ser Ser Pro Glu Lys Ile Glu Ile Leu Ala Pro Pro
225             230                 235                 240
Asn Gly Ser Val Pro Gly Asp Arg Ile Thr Phe Asp Ala Phe Pro Gly
            245                 250                 255
Glu Pro Asp Lys Glu Leu Asn Pro Lys Lys Lys Ile Trp Glu Gln Ile
        260                 265                 270
Gln Pro Asp Leu His Thr Asn Asp Glu Cys Val Ala Thr Tyr Lys Gly
        275                 280                 285
Val Pro Phe Glu Val Lys Gly Lys Gly Val Cys Arg Ala Gln Thr Met
    290                 295                 300
Ser Asn Ser Gly Ile Lys
305             310
```